US009226856B2

(12) United States Patent
Walsh et al.

(10) Patent No.: US 9,226,856 B2
(45) Date of Patent: Jan. 5, 2016

(54) INFLATABLE MEDICAL INTERFACES AND OTHER MEDICAL DEVICES, SYSTEMS, AND METHODS

(71) Applicant: Envision Diagnostics, Inc., El Segundo, CA (US)

(72) Inventors: Alexander C. Walsh, Los Angeles, CA (US); Paul G. Updike, Cerritos, CA (US); Richard Castro, Santa Monica, CA (US)

(73) Assignee: Envision Diagnostics, Inc., El Segundo, CA (US)

( * ) Notice: Subject to any disclaimer, the term of this patent is extended or adjusted under 35 U.S.C. 154(b) by 312 days.

(21) Appl. No.: 13/802,727

(22) Filed: Mar. 14, 2013

(65) Prior Publication Data

US 2014/0275935 A1 Sep. 18, 2014

(51) Int. Cl.
| | |
|---|---|
| G02C 7/04 | (2006.01) |
| G02C 1/00 | (2006.01) |
| G02C 3/00 | (2006.01) |
| G02C 5/00 | (2006.01) |
| A61F 9/02 | (2006.01) |
| A61B 3/10 | (2006.01) |
| A61B 3/16 | (2006.01) |
| A61B 5/00 | (2006.01) |

(52) U.S. Cl.
CPC ............... *A61F 9/026* (2013.01); *A61B 3/102* (2013.01); *A61B 3/165* (2013.01); *A61B 5/6803* (2013.01); *A61B 5/6843* (2013.01); *A61F 2250/0003* (2013.01)

(58) Field of Classification Search
CPC .............................. A61F 9/026; A61B 3/102
USPC ...................... 351/160 R, 158, 154, 155, 178
See application file for complete search history.

(56) References Cited

U.S. PATENT DOCUMENTS

| | | | |
|---|---|---|---|
| 4,154,114 | A | 5/1979 | Katz et al. |
| 4,237,901 | A | 12/1980 | Taenzer |
| 4,393,366 | A | 7/1983 | Hill |
| 4,479,931 | A | 10/1984 | Lambrecht et al. |
| 4,764,006 | A | 8/1988 | Hamano et al. |

(Continued)

FOREIGN PATENT DOCUMENTS

| | | |
|---|---|---|
| CA | 2595324 | 7/2006 |
| CA | 2678506 | 8/2008 |

(Continued)

OTHER PUBLICATIONS

US 8979269, 3/2015, Walsh et al. (withdrawn).

(Continued)

*Primary Examiner* — Brian Szmal
(74) *Attorney, Agent, or Firm* — Knobbe Martens Olson & Bear LLP

(57) ABSTRACT

An inflatable mask with two ocular cavities can seal against a user's face by forming an air-tight seal around the periphery of the user's eye socket. The sealed air-tight ocular cavity can be pressurized to take ocular measurements. The mask can conform to the contours of a user's face by inflating or deflating the mask. In addition, the distance between the user and a medical device (e.g. an optical coherence tomography instrument) can be adjusted by inflating or deflating the mask. Also disclosed herein is an electronic encounter portal and an automated eye examination. Other embodiments are also described.

29 Claims, 15 Drawing Sheets

(56) References Cited

U.S. PATENT DOCUMENTS

| | | |
|---|---|---|
| 4,848,340 A | 7/1989 | Bille et al. |
| 4,872,217 A | 10/1989 | Kitayama |
| 4,930,512 A | 6/1990 | Henriksen et al. |
| 5,005,966 A | 4/1991 | Handler et al. |
| 5,056,522 A | 10/1991 | Matsumura et al. |
| 5,141,302 A | 8/1992 | Arai et al. |
| 5,214,455 A | 5/1993 | Penney et al. |
| 5,369,454 A | 11/1994 | Reinstein et al. |
| 5,442,412 A | 8/1995 | Frey et al. |
| 5,491,524 A | 2/1996 | Hellmuth et al. |
| 5,493,109 A | 2/1996 | Wei et al. |
| 5,543,866 A | 8/1996 | Van de Velde |
| 5,557,350 A | 9/1996 | Yano |
| 5,776,068 A | 7/1998 | Silverman et al. |
| 5,914,772 A | 6/1999 | Dyer |
| 6,086,205 A | 7/2000 | Svetliza |
| 6,112,114 A | 8/2000 | Dreher |
| 6,293,674 B1 | 9/2001 | Huang et al. |
| 6,367,932 B1 | 4/2002 | Donaldson |
| 6,439,720 B1 | 8/2002 | Graves et al. |
| 6,450,643 B1 | 9/2002 | Wilson |
| 6,592,223 B1 | 7/2003 | Stern et al. |
| 6,609,794 B2 | 8/2003 | Levine |
| 6,619,799 B1 | 9/2003 | Blum et al. |
| 6,656,131 B2 | 12/2003 | Alster et al. |
| 6,687,389 B2 | 2/2004 | McCartney et al. |
| 6,692,436 B1 | 2/2004 | Bluth et al. |
| 6,705,726 B2 | 3/2004 | Tanassi et al. |
| 6,820,979 B1 | 11/2004 | Stark et al. |
| 6,939,298 B2 | 9/2005 | Brown et al. |
| 7,008,116 B2 | 3/2006 | Kobayashi et al. |
| 7,219,996 B2 | 5/2007 | Ichikawa |
| 7,233,312 B2 | 6/2007 | Stern et al. |
| 7,237,898 B1 | 7/2007 | Hohla et al. |
| 7,350,921 B2 | 4/2008 | Ridings |
| 7,370,966 B2 | 5/2008 | Fukuma et al. |
| 7,384,146 B2 | 6/2008 | Covannon et al. |
| 7,445,335 B2 | 11/2008 | Su et al. |
| 7,458,685 B2 | 12/2008 | Liang et al. |
| 7,549,752 B2 | 6/2009 | Peyman et al. |
| 7,614,747 B2 | 11/2009 | Foster |
| 7,618,372 B2 | 11/2009 | dela Houssaye |
| 7,744,221 B2 | 6/2010 | Wei et al. |
| 7,815,310 B2 | 10/2010 | Su et al. |
| 7,982,881 B2 | 7/2011 | Fercher et al. |
| 7,997,728 B2 | 8/2011 | Huang et al. |
| 8,002,410 B2 | 8/2011 | Shea |
| 8,079,711 B2 | 12/2011 | Stetson et al. |
| 8,100,530 B2 | 1/2012 | Zhou et al. |
| 8,348,429 B2 | 1/2013 | Walsh et al. |
| 8,372,411 B2 | 2/2013 | Meinke et al. |
| 8,381,729 B2 | 2/2013 | Freitag et al. |
| 8,820,931 B2 | 9/2014 | Walsh et al. |
| 2001/0025226 A1 | 9/2001 | Lavery |
| 2002/0021411 A1 | 2/2002 | Wilson |
| 2002/0080329 A1 | 6/2002 | Kasahara |
| 2002/0099305 A1 | 7/2002 | Fukushima et al. |
| 2003/0065636 A1 | 4/2003 | Peyrelevade |
| 2003/0232015 A1 | 12/2003 | Brown et al. |
| 2004/0019032 A1 | 1/2004 | North et al. |
| 2004/0036838 A1 | 2/2004 | Podoleanu et al. |
| 2004/0141152 A1 | 7/2004 | Marino et al. |
| 2004/0196432 A1 | 10/2004 | Su et al. |
| 2004/0254154 A1 | 12/2004 | Ashton |
| 2004/0260183 A1 | 12/2004 | Lambert et al. |
| 2005/0001980 A1 | 1/2005 | Spector |
| 2005/0041200 A1 | 2/2005 | Rich |
| 2005/0105044 A1 | 5/2005 | Warden et al. |
| 2005/0140981 A1 | 6/2005 | Waelti |
| 2006/0077347 A1 | 4/2006 | Liang et al. |
| 2006/0077348 A1 | 4/2006 | Gorin |
| 2006/0092376 A1 | 5/2006 | Baek et al. |
| 2006/0109423 A1 | 5/2006 | Wang |
| 2006/0119858 A1 | 6/2006 | Knighton et al. |
| 2006/0135859 A1 | 6/2006 | Iliff |
| 2006/0158655 A1 | 7/2006 | Everett et al. |
| 2006/0187462 A1 | 8/2006 | Srinivasan et al. |
| 2006/0195076 A1 | 8/2006 | Blumenkranz et al. |
| 2006/0257451 A1 | 11/2006 | Varner et al. |
| 2006/0290885 A1 | 12/2006 | Covannon et al. |
| 2007/0008116 A1 | 1/2007 | Bergman et al. |
| 2007/0024868 A1 | 2/2007 | Izatt et al. |
| 2007/0030450 A1 | 2/2007 | Liang et al. |
| 2007/0032782 A1 | 2/2007 | Youssefi et al. |
| 2007/0055222 A1 | 3/2007 | Hohla et al. |
| 2007/0073113 A1 | 3/2007 | Squilla et al. |
| 2007/0081165 A1 | 4/2007 | Kilic et al. |
| 2007/0081166 A1 | 4/2007 | Brown et al. |
| 2007/0153233 A1 | 7/2007 | Campin et al. |
| 2007/0177104 A1 | 8/2007 | Lacombe et al. |
| 2007/0195269 A1 | 8/2007 | Wei et al. |
| 2007/0216909 A1 | 9/2007 | Everett et al. |
| 2007/0273831 A1 | 11/2007 | Liang et al. |
| 2007/0282313 A1 | 12/2007 | Huang et al. |
| 2007/0287932 A1 | 12/2007 | Huang et al. |
| 2007/0291228 A1 | 12/2007 | Huang et al. |
| 2007/0291277 A1 | 12/2007 | Everett et al. |
| 2008/0007694 A1 | 1/2008 | Wei et al. |
| 2008/0106696 A1 | 5/2008 | Buckland et al. |
| 2009/0141240 A1 | 6/2009 | Weitz et al. |
| 2009/0153796 A1 | 6/2009 | Rabner |
| 2010/0100238 A1 | 4/2010 | Torian |
| 2010/0110377 A1 | 5/2010 | Maloca et al. |
| 2011/0299034 A1 | 12/2011 | Walsh et al. |
| 2013/0201449 A1 | 8/2013 | Walsh et al. |
| 2015/0085253 A1 | 3/2015 | Walsh |
| 2015/0138503 A1 | 5/2015 | Walsh |

FOREIGN PATENT DOCUMENTS

| | | |
|---|---|---|
| CN | 1593329 A | 3/2005 |
| CN | 101049229 A | 10/2007 |
| CN | 200 980 154 Y | 11/2007 |
| CN | 201 491 234 U | 5/2010 |
| CN | 201 586 123 | 9/2010 |
| DE | 10 2005 058220 | 6/2007 |
| EP | 0 697 611 | 2/1996 |
| EP | 1 775 545 | 4/2007 |
| EP | 1 858 402 | 11/2007 |
| EP | 1 864 608 | 12/2007 |
| EP | 2 124 713 | 12/2009 |
| JP | S 57-29204 | 2/1982 |
| JP | S 57-153635 | 9/1982 |
| JP | 05-220113 | 8/1993 |
| JP | 11-225958 | 8/1999 |
| JP | 2004-528111 | 9/2004 |
| JP | 2005-83954 | 3/2005 |
| JP | 2005-531346 | 11/2005 |
| WO | WO 99/57507 | 11/1999 |
| WO | WO 02/088684 | 11/2002 |
| WO | WO 2004/002298 | 1/2004 |
| WO | WO 2006/078802 | 7/2006 |
| WO | WO 2007/065493 | 6/2007 |
| WO | WO 2007/139927 | 12/2007 |
| WO | WO 2007/142960 | 12/2007 |
| WO | WO 2008/101359 | 8/2008 |
| WO | WO 2009/095473 | 8/2009 |
| WO | WO 2009/128912 | 10/2009 |
| WO | WO 2009/131701 | 10/2009 |
| WO | WO 2010009450 | 1/2010 |
| WO | WO 2010117386 | 10/2010 |
| WO | WO 2014/158658 | 1/2015 |

OTHER PUBLICATIONS

"3D OCT-1000 | Topcon," Press Release Mar. 31, 2008, available from internet at http://www.topcon.co.jp/news/20080331-508.html, site visited Apr. 14, 2015.

"A New Level for Retinal Imaging: Topcon's 3D OCT-1000," Vision Care Product New Nov./Dec. 2007 pp. 1-2.

"Topcon Medical Systems Releases 3D OCT-1000 TrueMap™ Software Version 2.12," Topcon Press Release Feb. 8, 2008, pp. 1-2.

(56) References Cited

OTHER PUBLICATIONS

Bachmann, et al., Heterodyne Fourier domain optical coherence tomography for full range probing with high axial resolution; Optics Express; vol. 14; Issue No. 4; pp. 1487-1496, Feb. 20, 2006.

Bigelow, et al., Compact multimodal adaptive-optics spectral-domain optical coherence tomography instrument for retinal imaging; J.Opt. Soc., Am. A.; vol. 24; Issue No. 5; pp. 1327-1336, May 2007.

Bowd, C., et al., "Bayesian Machine Learning Classifiers for Combining Structural and Functional Measurements to Classify Healthy and Glaucomatous Eyes," Investigative Ophthalmology & Visual Science, Mar. 2008, 49(3): 945-953.

Boyer, K.L., et al. "Automatic Recovery of the Optic Nervehead Geometry in Optical Coherence Tomography," IEEE Transactions on Medical Imaging, May 2006, 25(5): 553-570.

Brochure for Optical Coherence Tomography 3D OCT-1000 Mark II, in 11 pages. Copyright 2008.

Bu, et al., Full-range parallel Fourier-domain optical coherence tomography using sinusoidal phase-modulating interferometry; Journal of Optics A: Pure and Applied Optics; vol. 9; pp. 422-426, Mar. 2007.

Burgansky-Eliash, et al., Optical Coherence Tomography Machine Learning Classifiers for Glaucoma Detection: A Preliminary Study, Investigative Ophthalmology & Visual Science; vol. 46; No. 11; pp. 4147-4152, Nov. 2005.

Chang, et al.; New developments in optical coherence tomography for glaucoma, Current Opinion in Ophthalmology; vol. 19; Issue No. 2; pp. 127-135; Mar. 2008.

Drexler, et al., State-of-the-art retinal optical coherence tomography; Progress in Retinal and Eye Research; vol. 27; Issue 1; pp. 45-88; Jan. 2008.

Fernandez, Delineating Fluid-Filled Region Boundaries in Optical Coherence Tomography Images ofthe Retina; IEEE Transactions on Medical Imaging; vol. 24; Issue No. 8; pp. 929-945, Aug. 2005.

Ghosn, et al., Nondestructive Quantification of Analyte Diffusion in Cornea and Sclera Using Optical Coherence Tomography; investigative Ophthalmology & Visual Science; vol. 48, No. 6, pp. 2726-2733, Jun. 2007.

Guo, et al., En face optical coherence tomography: a new method to analyse structural changes of the optic nerve head in rat glaucoma, British Journal of Ophthalmology, Sep. 2005, vol. 89, Issue 9, pp. 1210-1216.

Huang, et al., Development and Comparison of Automated Classifiers for Glaucoma Diagnosis Using Stratus Optical Coherence Tomography; Investigative Ophthalmology & Visual Science; vol. 46; Issue No. 11; pp. 4121-4129, Nov. 2005.

Keystone View; Computer Controlled vision Screeners. http://www.keystoneview.com?p=cv&id=39, 2 pages, 2003.

Koizumi, et al: "Three-Dimensional Evaluation of Vitreomacular Traction and Epiretinal Membrane Using Spectral-Domain Optical Coherence Tomography," American Journal of Ophthalmology, Ophthalmic Publ, Chicago, IL, US, vol. 145, No. 3, Mar. 2008, pp. 509-517.el.

Koozekanani, et al., Retinal Thickness Measurements from Optical Coherence Tomography Using a Markov Boundary Model. IEEE Transactions on Medical Imaging; vol. 20; No. 9; pp. 900-916, Sep. 2001.

Lavanya, et al, Screening for Narrow Angles in the Singapore Population: Evaluation of New Noncontact Screening Methods; vol. 115; Issue No. 10, pp. 1720-1727e2, Oct. 2008.

Manassakorn, et al., Comparison of Retinal Nerve Fiber Layer Thickness and Optic Disk Algorithms with Optical Coherence Tomography to Detect Glaucoma; Am J Ophthalmol; vol. No. 141; pp. 105-115; Jan. 2006.

Parikh, M.D., et al., Diagnostic Capability of Optical Coherence Tomography (Stratus OCT 3) in Early Glaucoma; American Academy of Ophthalmology; pp. 2238-2243, vol. 114, Issue No. 12, Dec. 2007.

Prevent Blindness America. Sure Sight Vision Screener. Prevent Blindness Tri-State. http://wwww.preventblindness.org/tristate/suresight.htrnl, 2 pages, 2006.

Sadda, Srinivas R., et al., Automated Detection of Clinically Significant Macular Edema by Grid Scanning Optical Coherence Tomography. American Academy of Ophthalmology, vol. 113, No. 7, pp. 1187 e.I-1187 e.12, Jul. 2006.

Sarunic, et al., "New Imaging Device Can Detect Glaucoma Risk", Duke Medicine News and Communications, Jun. 2008.

Stein, et al., A new quality assessment parameter for optical coherence tomography; British Journal of Ophthalmology; vol. 90; Issue No. 2 pp. 186-190; Feb. 2006.

Stereo Optical Co., Inc. The Optec® 5500/5500P—The Industry Standard for Visual Screening and Vision Testing Devices. http://www.stereooptical.com/html/optec-5500.html, 3 pages, 2007.

Stereo Optical Co., Inc. The Optec® Functional Vision Analyzer™— Contrast Sensitivity Tests with Two Glare Levels Under Four Testing Conditions. http://www.stereooptical.com/htrnl/functional_vision_analyzer.html, 3 pages, 2007.

STRATUS OCT™ Software version 4.0 Real Answers in Real Time. [Online] Jan. 2006, XP002530105 Retrieved from the Internet: URL: http://www.meditec.zeiss.com/88256DE3007B916B/0/C26634DOCFF04511882571BI005DECFD/$file/stratusocLen.pdf>[retrieved on May 28, 2009] the whole document.

Topcon Medical Systems Receives FDA Clearance to Market the 3D OCT-1000, the World's First Combination of Fourier Domain OCT and a Color Non-Mydriatic Retinal Camera, Topcon Press Release Jul. 2, 2007, pp. 1-2.

Topcon Optical Coherence Tomography 3D OCT-1000 Brochure, 7 pages, 2008.

Vakhtin, et al, Common-path interferometer for frequency-domain optical coherence tomography; Applied Optics; vol. 42, Issue No. 34; pp. 6953-6958, Dec. 1, 2003.

Vakhtin, et al., Demonstration of complex-conjugate-resolved harmonic Fourier-domain optical coherence tomography imaging of biological samples; Applied Optics; vol. 46; Issue No. 18; pp. 3870-3877, Jun. 20, 2007.

Walsh, A. "3D-OCT in the Evaluation of Retinal Disease," Highlights of Ophthalmology, Jul. 2006, 34(3): 9-10.

Walsh, A. M.D., "Next-generation OCT: What to Look for in a Fourier Domain OCT Instrument," Retinal Physician, pp. 1-6, May 1, 2007.

Xu, et al., Anterior Chamber Depth and Chamber Angle and Their Associations with Ocular and General Parameters: The Beijing Eye Study. American Journal of Ophthalmology, vol. 145, pp. 929-936el, May 2008.

Yasuno, et al., One-shot-phase-shifting Fourier domain optical coherence tomography by reference wavefront tilting; Optics Express; vol. 12; Issue No. 25; pp. 6184-6191, Dec. 13, 2004.

Zhang, et al., Full range polarization-sensitive Fourier domain optical coherence tomography; Optics Express; vol. 12; Issue No. 24; pp. 6033-6039, Nov. 29, 2004.

Zhou et al., "Biometric measurement of the mouse eye using optical coherence tomography with focal plane advancement", Vision Research, Apr. 2008, vol. 48, pp. 1137-1143.

International Search Report and Written Opinion, re PCT/US2014/019150, mailed Dec. 4, 2014.

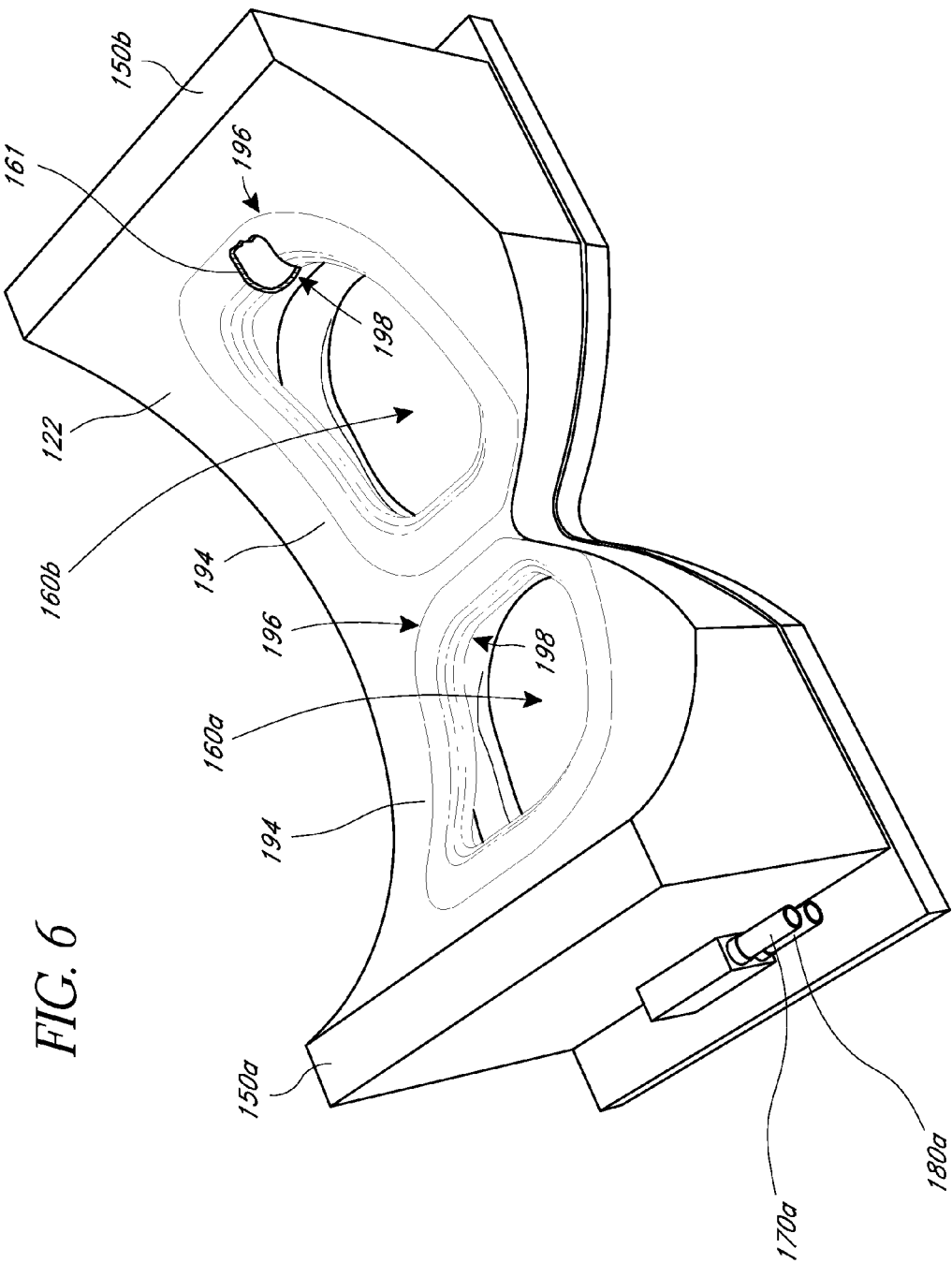

INFLATABLE MEDICAL INTERFACES AND OTHER MEDICAL DEVICES, SYSTEMS, AND METHODS

BACKGROUND OF THE INVENTION

1. Field of the Invention

Embodiments of the invention relate to the field of healthcare, including for example, devices, systems, methods of automating the provision of diagnostic healthcare services to a patient as part of an examination meant to detect disorders or diseases. In some but not all instances, these healthcare services may apply only to eye care encounters, exams, services and eye diseases.

2. Description of the Related Art

Many people visiting medical offices often use the same equipment. Cross-contamination has become a problem of increasing concern, especially during certain periods such as flu season. As the provision of healthcare becomes more automated, fewer office personnel may be present to clean devices between uses. Accordingly systems and methods for improving hygiene are desirable.

SUMMARY OF THE INVENTION

A wide range of embodiments are described herein. In some embodiments, a mask may comprise a distal sheet member having one or more substantially optically transparent sections and a proximal inflatable member having a generally rear concaved surface that may face a first patient's face when in use. The rear concaved surface may be configured to conform to contours of the first patient's face. The inflatable member may have two cavities therein. The two cavities may be generally aligned with the one or more substantially optically transparent sections, and may extend from the rear concaved surface toward the distal sheet member such that the cavities define two openings on the rear concave surface. The rear concave surface may be configured to seal against the first patient's face such that the first patient's eyes align with the two cavities, so that the rear concave surface forms seals around a peripheral region of the first patient's eye sockets that inhibit flow of fluid into and out of the cavities. The mask may further comprise an ocular port providing access to at least one of the two ocular cavities for fluid flow into and out of the at least one of the two ocular cavities and an inflation port providing access to inflate the inflatable member.

In various embodiments, the rear concaved surface may be configured to conform to the contours of the first patient's face with inflation of the inflatable member via the inflation port. The inflatable member may be underinflated and the rear concaved surface may be configured to conform to the contours of the first patient's face with inflation of the underinflated inflatable member via the inflation port. The rear concaved surface may be configured to conform to the contours of the first patient's face with application of negative pressure to the inflatable member via the inflation port. The mask may further comprise particulate matter disposed within the inflatable member. The particulate matter may be configured to pack together with application of a negative pressure to the inflatable member via the inflation port, so that the rear concaved surface conforms to the contours of the first patient's face.

In various embodiments, the rear concaved surface may be configured to conform to contours of a second patient's face, wherein a contour of the second patient's face is different from a contour of the first patient's face. The seals may be air-tight. The mask may further comprise a lip extending into at least one of the two cavities from a perimeter of at least one of the two openings, the lip having distal ends curving toward the distal sheet member in a default position, the distal ends configured to move rearwardly such that the lip seals against the user's face upon introduction of positive pressure into the at least one of the two cavities. The inflatable member may be opaque.

In various embodiments, the distal sheet may be configured to interface with a medical device, which may be an eye exam device. The mask may be configured to couple with a docking portion on a medical device. The mask may be configured to couple with the docking portion via a flange that slides into a slot of the docking portion. The inflation port and the ocular port of the mask may be configured to couple with conduit ends on a medical device. The ocular port and the inflation port may include a male portion, wherein the conduit ends on the medical device include a female portion configured to slidably receive the male portion. The ocular port and the inflation port may be configured to couple with the conduit ends on the medical device substantially simultaneously.

Some embodiments of the invention relate to the utilization of devices that replace, augment or enhance human laborers in a clinical health care setting. These devices may be used alone or in conjunction with other devices used in exams such as exams of the eye.

For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIG. 6 schematically illustrates a perspective view of another embodiment of a mask with a seal around the ocular cavities.

DETAILED DESCRIPTION OF THE PREFERRED EMBODIMENT

Some embodiments disclosed herein provide an inflatable mask that can interface with medical devices, such as medical diagnostic devices, such as optical coherence tomography ("OCT") devices. The inflatable mask can serve a variety of purposes, including maintaining a barrier between the patient and the medical device to ensure cleanliness and hygiene, providing comfort to the patient, and stabilizing the patient's location with respect to the machine. In some embodiments, the inflatable mask can form air-tight ocular cavities around the patient's eyes, allowing for pressurization of the ocular cavities, in order to obtain ocular measurements. Additionally, various embodiments of an automatic portal system and an automated eye examination are disclosed herein.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the embodiments of the inventions herein described.

Inflatable Medical Interface

Figure 1:
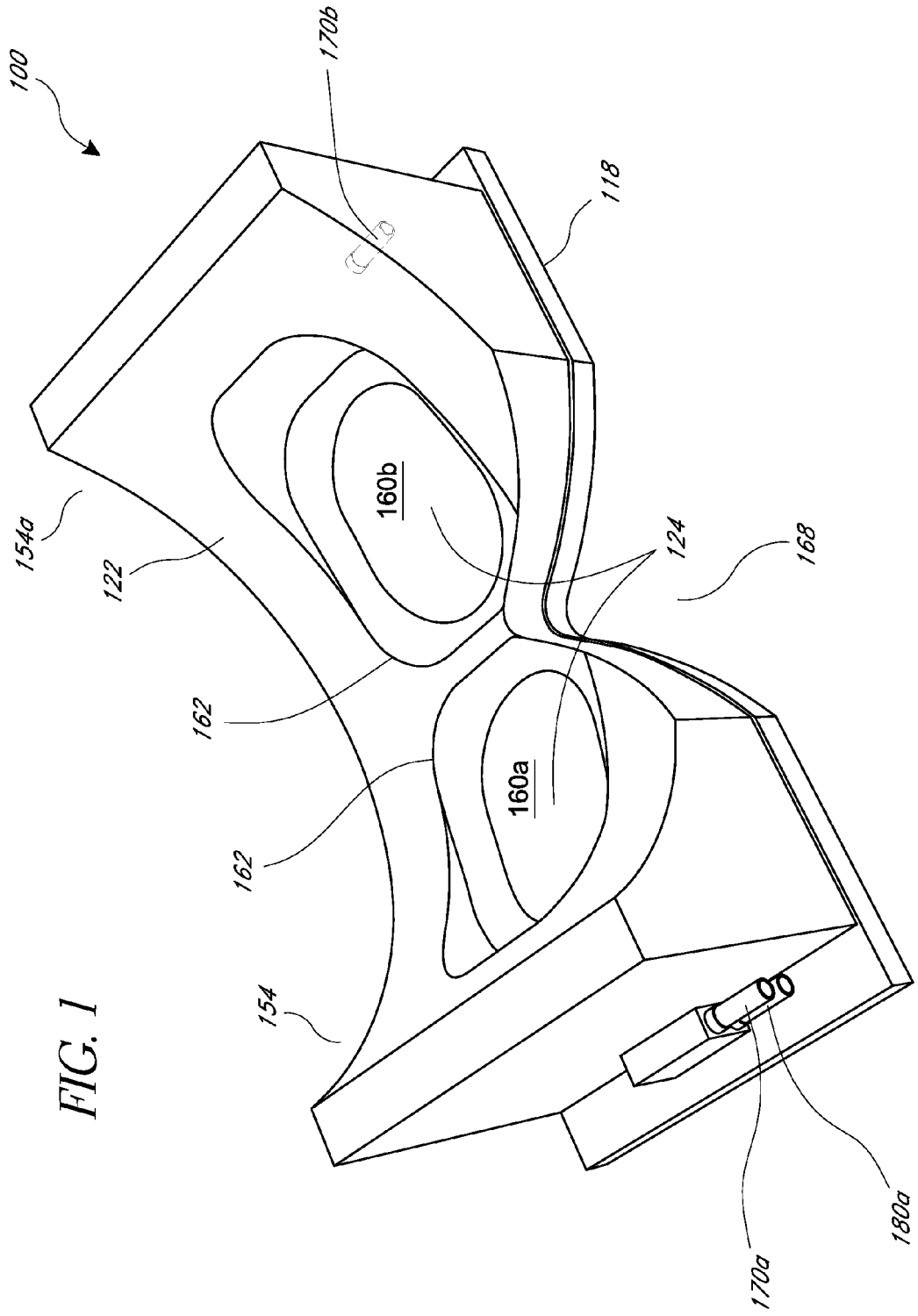
FIG. 1 schematically illustrates a perspective view of one embodiment of a mask which is inflatable and includes a framework that forms two cavities for the oculars.

Referring to FIG. 1, in one embodiment, a mask 100 includes a distal sheet member 118 which has optically transparent sections 124, and a proximal inflatable member 154 having a generally concaved rear surface 122. In use, the rear concaved surface 122 faces the patient's face and conforms to the patient's face, according to some embodiments of the invention. As used herein the terms "user" or "patient" or "subject" or "wearer" may be used interchangeably. Still Referring to FIG. 1, the inflatable member 154 can have two cavities 160a, 160b which are aligned with the optically transparent sections 124. In some embodiments, the cavities 160a, 160b extend from a distal sheet 118 to the rear concave surface 122 and define two openings 162 on the rear concave surface 122. In use, the patient's eyes align with the two cavities 160a, 160b, so that the rear concave surface 122 forms seals around the patient's eye sockets or face, e.g. forehead and cheeks, inhibiting flow of fluid into and out of the cavities 160a, 160b. In addition, the mask 100 can include ports 170a-b, 180a-b which provide access to control flow of fluid (e.g. air) into and out of the cavities 160a, 160b.

Figure 2A:
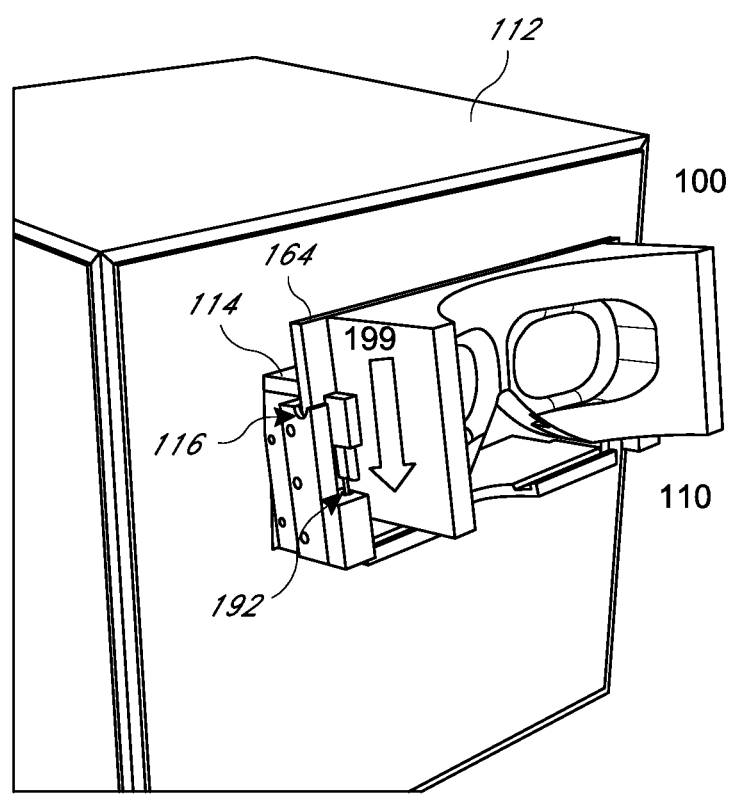
FIGS. 2a-2b schematically illustrates a mask removably attached to a medical device.
Figure 2B:
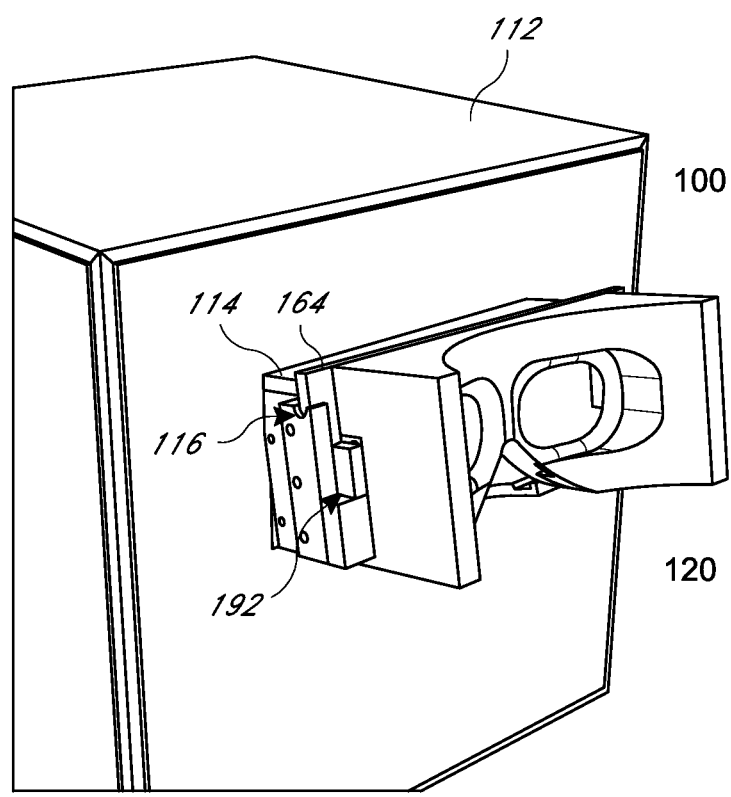

In some embodiments, the mask 100 can interface with a medical device. With reference to FIGS. 2a-2b, there is illustrated one embodiment whereby the mask 100 is placed on a separate device 112. In some embodiments, the separate device 112 is a medical device, such as a diagnostic or therapeutic device. In some embodiments, the separate device 112 is an ophthalmic device, such as a device for the eye, and may be an optical coherence tomography device ("OCT") that may contain a housing and instrumentation contained therein. The mask 100 may be used with a wide range of medical devices 112, such as for example an OCT device such as disclosed herein, as well as other OCT devices and other medical devices 112. In some embodiments, the medical device 112 can receive and removably connect to the mask 100. The mask 100 can be configured to connect to the medical device 112, adhere to one or more surfaces of the medical device 112, or be mechanically fixed to the medical device 112, or be secured to the medical device 112 in any other way (e.g. clamps, straps, pins, screws, hinges, elastic bands, buttons, etc.), such that the mask 100 is removable from the medical device 112 without damaging the mask 100.

In one embodiment, a docking portion 114, which may include an optical interface such as for example a plate, can be included on the medical device 112. The docking portion 114 can also include a slot 116 for receiving a mask 100. In some embodiments, the mask 100 includes a flange 164 that extends laterally outward past a side of the inflatable member 154 on the distal sheet 118 for slideably engaging with the slot 116. The mask 100 can be inserted into the slot 116 and slide down to a final locking position 120. In another embodiment, the flange 164 can be on the medical device 112 and the slot 116 can be on the mask 100.

Figure 3:
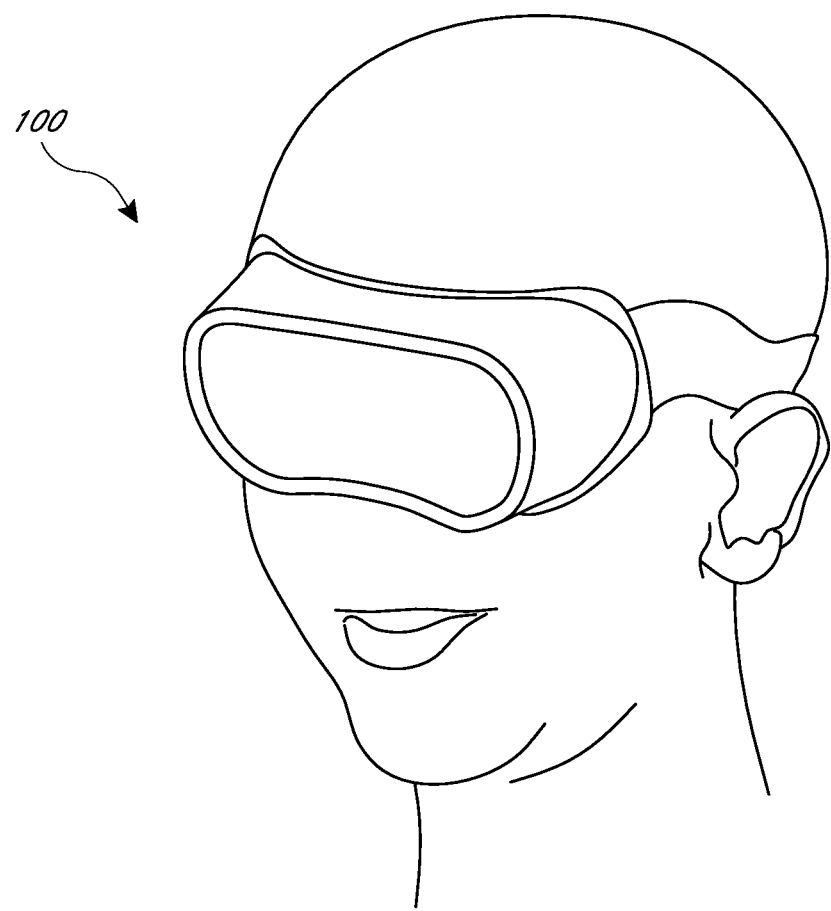
FIG. 3 schematically illustrates a user wearing a mask that provides, for example, an interface to a medical device such as a diagnostic device that is used by many patients.

With reference to FIG. 3, there is illustrated an example of a mask 100 worn by a user over the user's eyes. In various embodiments, the mask 100 may be removably attached to the wearer with an adhesive, an elastic band, a Velcro band, a strap, a buckle, a clip, and/or any other suitable fastener or mechanism. In some embodiments, the mask 100 can include mechanisms for both attaching to the wearer and attaching to the medical device 112. In other embodiments, a patient may use the mask 100 without any straps, bands, etc. that attach to the user. For example, referring to FIGS. 2a-b, the patient may simply move his/her face in alignment and in contact with the mask 100, which is secured to the medical device 112. In another embodiment, a patient who has a mask 100 secured to his/her face may position himself/herself properly with respect to the medical device 112, so that the distal sheet 118 interfaces with the medical device, 112, and the medical device 112 can take readings.

Figure 4:
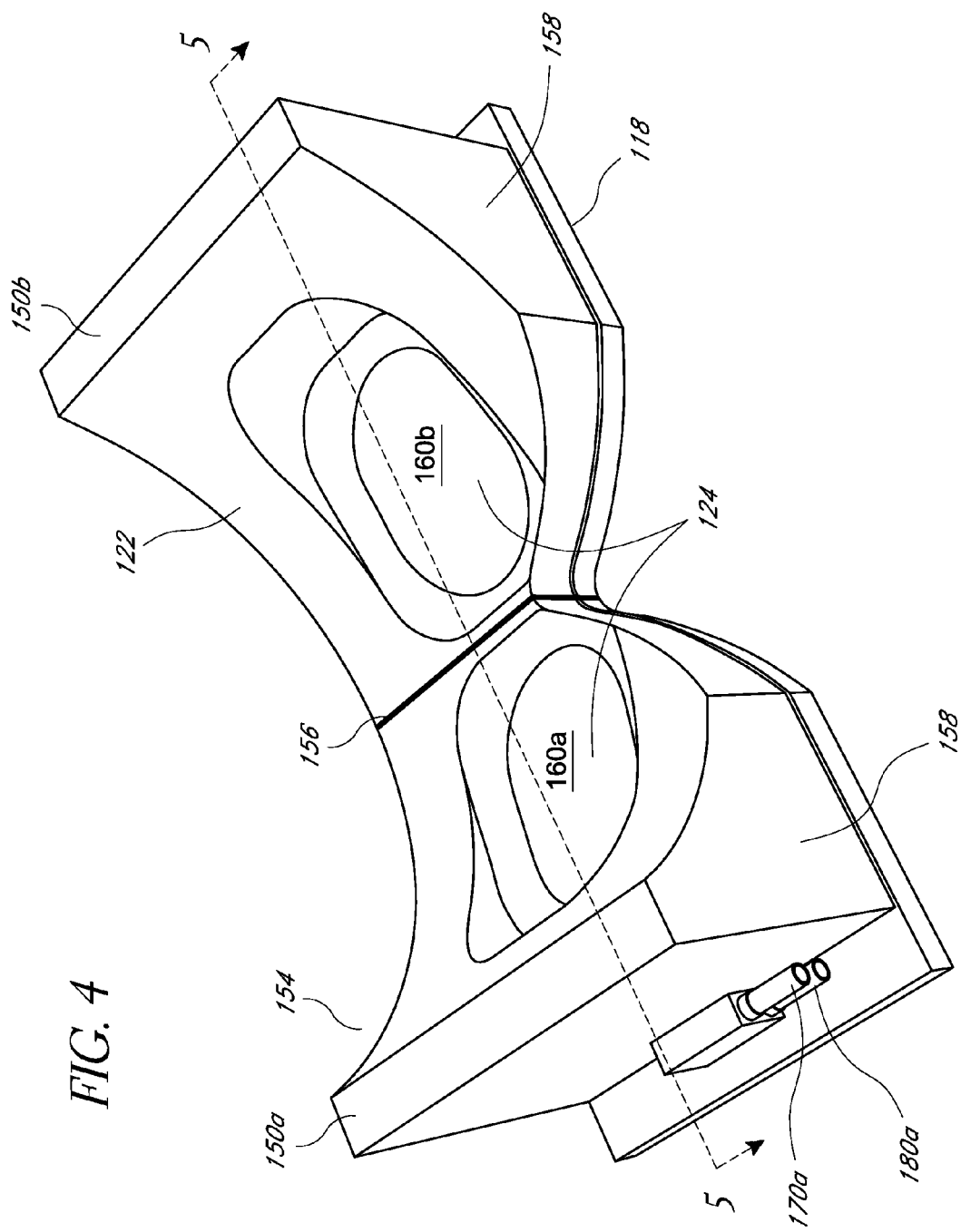
FIG. 4 schematically illustrates a perspective view of another embodiment of a mask with an inflatable framework that is partitioned into two separately inflatable sections.

Returning to FIG. 1, one embodiment of the mask 100 comprises an inflatable framework 154 having an inflatable chamber 154a, two cavities 160a, 160b, a frontward surface formed by a distal sheet member 118, and a rearward surface 122. It will be understood that "inflatable," as used herein, can include "deflatable," and vice versa. Thus, in some embodiments, an "inflatable" framework 154 or chamber 154a can be deflatable, and a "deflatable" framework 154 or chamber 154a can be inflatable. Referring to FIG. 1, cavities 160a, 160b may extend between the distal sheet member 118 and the rearward surface 122. In some embodiments, the frontward member 118 includes a window member 124, which can be substantially optically transparent in some embodiments, with minimal to no effects on the optics of a medical device 112 (e.g. an OCT device) which can interface with the mask 100, although some embodiments may introduce optical effects. In some embodiments, the distal sheet member 118 can be rigid. In some embodiments, the distal sheet member 118 can be made of polycarbonate, poly(methyl methacrylate), or glass. Other materials can be used. In other embodiments, the distal sheet member 118 can be flexible. The distal sheet member 118 can have a thickness of less than 0.1 mm, 0.1 mm, 0.5 mm, 1 mm, 2 mm, 4 mm, or more. In one embodiment, the window member 124 may be adjacent to the inflatable framework 154. Thus, the window member 124 may form a frontward surface of a cavity 160a, 160b. Further, the window member 124 may be aligned with the cavities 160a, 160b. In addition, the cavities 160a, 160b can define openings on the rearward surface, defined by perimeters 162. Referring to FIG. 4, the inflatable framework 154 can have two separately inflatable chambers 150a, 150b. Still referring to FIG. 4, in one embodiment, one inflatable chamber 150a can have a cavity 160a therein, and another inflatable chamber 150b can have another cavity 160b therein.

The distal sheet member 118 may be substantially flat and the rearward surface 122 may be generally curved and concave according to one embodiment of the invention. Referring to FIG. 4, in one embodiment the thickness of the mask 100 is thinnest at the center 156 and thickest toward the outer edges 158, with the thickness decreasing from the outer edges 158 toward the center 156, thereby defining a curved and concave rearward surface 122.

During use, a patient's face is brought in contact with the rearward surface 122 of the mask, such that the patient's eyes are aligned with the cavities 160a, 160b, and the patient "sees" into the cavities 160a, 160b. Thus in some embodiments, the cavities 160a, 160b may be referred to as ocular cavities 160a, 160b. In one embodiment, only the portion of the distal sheet member 118 that aligns with the patient's eyes may be optically transparent, with other portions opaque or non-transparent.

In some embodiments, the rear concaved surface 122 of the mask 100 can seal against a patient's face around the general area surrounding the patient's eyes sockets, thereby forming a seal around the patient's eye sockets. The seal may be air-tight and liquid-tight according to some embodiments of the invention. In some embodiments, a seal may be formed between the user and the mask 100 without the need for assistance from additional personnel. In some embodiments, various portions of the patient's face can form the seal around the ocular cavities 160a, 160b. For example, the patient's forehead, cheekbones, and/or nasal bridge (e.g. frontal bone, supraorbital foramen, zygomatic bone, maxilla, nasal bone) can form a seal around the ocular cavities 160a, 160b. As used herein, reference to a "peripheral region" around the eye socket shall refer to any combination of the above.

Figure 5:
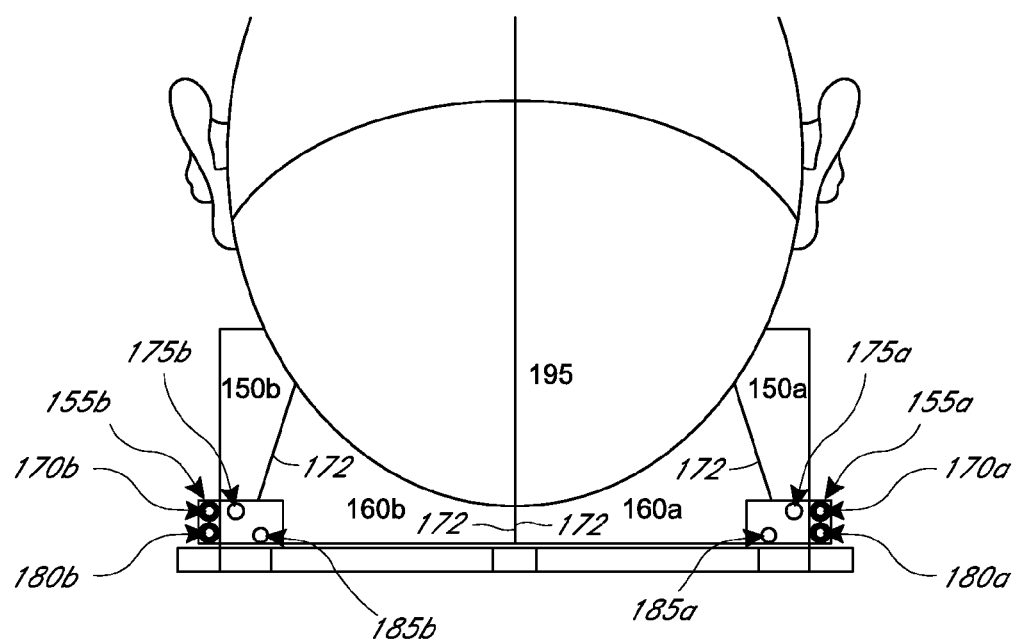
FIG. 5 schematically illustrates a cross section of the mask in FIG. 4 taken along the lines 5-5.

FIG. 5 illustrates a top view of a patient wearing a mask 100. The mask 100 in FIG. 5 is a cross-section of the mask 100 taken along line 5-5 in FIG. 4. Referring to FIG. 5, as seen from the view of the patient, the mask 100 comprises a right cavity 160b, such as a right ocular right cavity, a left cavity 160a, such as a left ocular cavity, a right inflatable chamber 150b, and a left inflatable chamber 150b. The walls 172 of the ocular cavities 160a, 160b, the window members 124, and the head of the user 195 may form an air-tight enclosed area. The head of the user 195 (e.g. the peripheral region around the user's eye sockets) forms a seal with the rearward perimeters 162 of the cavities 160a, 160b, thus allowing the cavities 160a, 160b to hold air or fluid. This seal may be capable of holding air or fluid pressures of, for example, 0.5 psi, 1 psi, or 5 psi or pressures therebetween. Higher or lower pressures are also possible.

Still referring to FIG. 5, some embodiments of the invention include inlet assemblies 155a, 155b. The inlet assemblies may include ports 170a-b, 180a-b, allowing access to the inflatable chambers 150a, 150b, and/or the cavities 160a, 160b.

Air, fluid, and/or other substances can be introduced into the ocular cavities 160a, 160b, via ports 180a, 180b, 185a, 185b. Air may be introduced into the left ocular cavity 160a by supplying an air source (e.g. via a pump) to the port at 180a. Thus, following the path of the air, the air may enter the port at 180a, then exit the port at 185a and into the left ocular cavity 160a (180a and 185b represent two ends of the same path). Similarly, regarding the right ocular cavity 160b, air may enter the port at 180b, then exit the port at 185b and into the right ocular cavity 160b.

Accordingly, in some embodiments, pressure inside the ocular cavities 160a, 160b may be controlled by adjusting the amount of air into and out of the ports 180a, 180b. Further, the air tight seal formed between the patient's face and the mask 100 can prevent unwanted leaks into or out of the ocular cavities 160a, 160b. This can be advantageous when air or fluid is used to challenge or test a body function. For example, air pumped into sealed air chamber cavities 160a, 160b in front of the eye can create positive pressure which can be used to press on the eye for the purposes of measuring the force of globe retropulsion or measuring intraocular pressure. In addition, air can be directed to the cornea, which is imaged with OCT. In some embodiments, air is pumped into the ocular cavities 160a, 160b to achieve a pressure of up to 1-2 psi. In some embodiments, the air supplied to the ocular cavities 160a, 160b is supplied by ambient surroundings, such as the ambient air in a clinical room using for example a pump.

In some embodiments, chamber ports 170a, 170b, 175a, 175b provide access to inflatable chambers 150a, 150b for inflating or deflating the chambers 150a, 150b. The chambers 150a, 150b may be inflated by introducing an air source (e.g. via a pump) to the ports at 170a, 180a. Thus, for example, following the path of the air, the air may enter the port at 170a, then exit the port at 175a and into the left inflatable chamber 150a, thereby inflating that chamber 150a. The right chamber 150b may be inflated in a similar manner. Negative pressure (e.g. a vacuum) can be applied to the ports 170a, 170b connected to the inflatable chambers 150a, 150b, thereby deflating the chambers 150a, 150b. As used herein, "deflating" shall include applying negative pressure.

In some embodiments, inflating the chambers 150a, 150b can cause the mask 100 to conform to the contours of a user's face. In addition, deflating the chambers 150a, 150b can cause the mask 100 to conform to the contours of a user's face. Further, inflating or deflating the chambers 150a, 150b can adjust a thickness of the mask 100, thus changing the distance between a user (who may face the rear concaved surface 122) and a medical device 112 (which may be interfaced with the distal sheet member 118).

In various embodiments, a port 170a-b, 180a-b is provided for each chamber 150a, 150b and cavity 160a, 160b. For example, referring to FIG. 5, there is illustrated a port 185b for the right cavity, a port 175b for the right inflatable chamber 150b, a port 185a for the left cavity 160a, and a port 175a for the left inflatable chamber 150a.

In one embodiment, two ports may be provided for one inflatable framework 154. For example, returning to FIG. 1, one port 170b is provided on the right side of the inflatable framework 154, and another port 170a is provided on the left side of the inflatable framework 154. Providing two ports for one chamber 154 can help to equalize the distribution of substances (e.g. air or fluid) in the chamber 154 by allowing access to the chamber 154 at different regions.

In one embodiment, the inflatable framework 154 does not include any ports. For example, the inflatable framework 154 may be pre-formed as desired, by filling it with a desired volume of fluid or air. Ports 170a-b, 180a-b may be added, removed, arranged, or configured in any suitable manner.

In some embodiments, the mask 100 advantageously can conform to a patient's face, thereby allowing the formation of a complete air-tight seal between the peripheral region around a user's eye sockets and the rear concaved surface 122 around the ocular cavities 160a, 160b. Accordingly, the rearward perimeter 162 of the cavities 160a, 160b can be configured to sealingly engage a periphery of a patient's eye socket. In some embodiments, the mask 100 includes a recess 168 (see e.g. FIGS. 1, 4, 6), allowing room for a patient's nose, so that the mask 100 forms a seal against the parts of a patient's face with a lower degree of curvature, increasing the surface area of the patient's face to which the mask 100 conforms.

In one embodiment, the air-tight seal can be formed by inflating the inflatable framework 154. In some embodiments, the inflatable framework 154 can resemble a bag. In some embodiments, a mask 100 with a relatively deflated framework 154 is provided to a patient. Because the bag 154 is deflated, it may exhibit some "slack." The patient's face may be brought in contact with the mask 100, and then the bag 154 may be inflated, causing the bag 154 to inflate around the contours of the patient's face and thereby conform to the patient's face. Accordingly, a complete air-tight seal can be formed between the patient's face and the rear concaved surface 122 around the ocular cavities 160a, 160b. The bag 154 may be inflated by introducing air, gas, fluid, gel, or any other suitable substance. In addition, the bag 154 can be deflated, causing the mask 100 to disengage from the patient's face, according to one embodiment of the invention.

In one embodiment, an air-tight seal is formed by applying a vacuum to the inflatable framework 154. In some embodiments, when the framework 154 is filled with particulate matter, such as coffee grounds, a plasmoid transformation to a semi-solid but form-fitting filler can be achieved by subjecting the particulate matter to a vacuum. For example, the framework 154 can be molded into shape easily when particulate matter is loosely contained in the framework 154, similar to a bean bag. A patient's face may then be brought into contact with the mask 100. Applying a vacuum to the bag 154 causes the particulate matter to pack tightly, thereby causing the bag 154 to conform to the contours of a patient's face. The tightly packed particulate matter can thus undergo a plasmoid transformation to a solid, while still allowing the framework 154 to conform to the patient's face and create an air-tight seal.

To facilitate the seal between a patient and the cavities 160a, 160b, the mask 100 can be configured with a lip 194 around the perimeter 162 of a cavity 160a, 160b, as illustrated in FIG. 6. FIG. 6 illustrates a lip 194 with a cut-away portion 161 showing the curvature of the lip 194. In one embodiment, the lip 194 comprises a first end 196 attached to the perimeter 162 of the cavity 160a, 160b and a second end 198 extending partially into the cavity 160a, 160b. In one embodiment, the edge 198 of the lip 194 may extend more or less and curl inward, as illustrated in FIG. 6. In one embodiment, the first end 196 and second end 198 define a curve, such that the lip 194 curls inwardly partially into the cavity 160a, 160b. Further, the lip 194 can be flexible and configured to extend in a rearward direction (e.g. toward the rearward surface 122). Thus, when pressure is introduced inside the cavity 160a, 160b, and pressure exerts a force in a rearward direction, the lip 194 can move rearwardly. When the inflatable framework 154 is sealed with a peripheral region around a user's eye socket, and the lip 194 moves rearwardly, the lip 194 can seal against the user's eye socket, preventing pressure from escaping.

In some embodiments, the mask 100 can be configured to be comfortable by filling the chambers 160a, 160b with soft gel fillers, particulate fillers such as foam beads or sand, or air fillers.

In one embodiment, the mask 100 can be custom made to fit the specific patient using it. For example, the mask 100 may be molded for a specific patient in a clinic. Thus, the mask 100 can be uniquely customized for a particular patient according to one embodiment. In another embodiment, the mask 100 is a "one size fits all" mask 100. Other embodiments are possible, including differential sizing based on age, height or facial structure. In some embodiments, the mask 100 is pre-inflated. In addition, air-tight seals can be formed between the rear curved surface 122 of the mask around the ocular cavities 160a, 160b and the peripheral region around a patient's eye sockets (e.g. via a lip) when the mask 100 is pre-inflated.

Figure 7A:
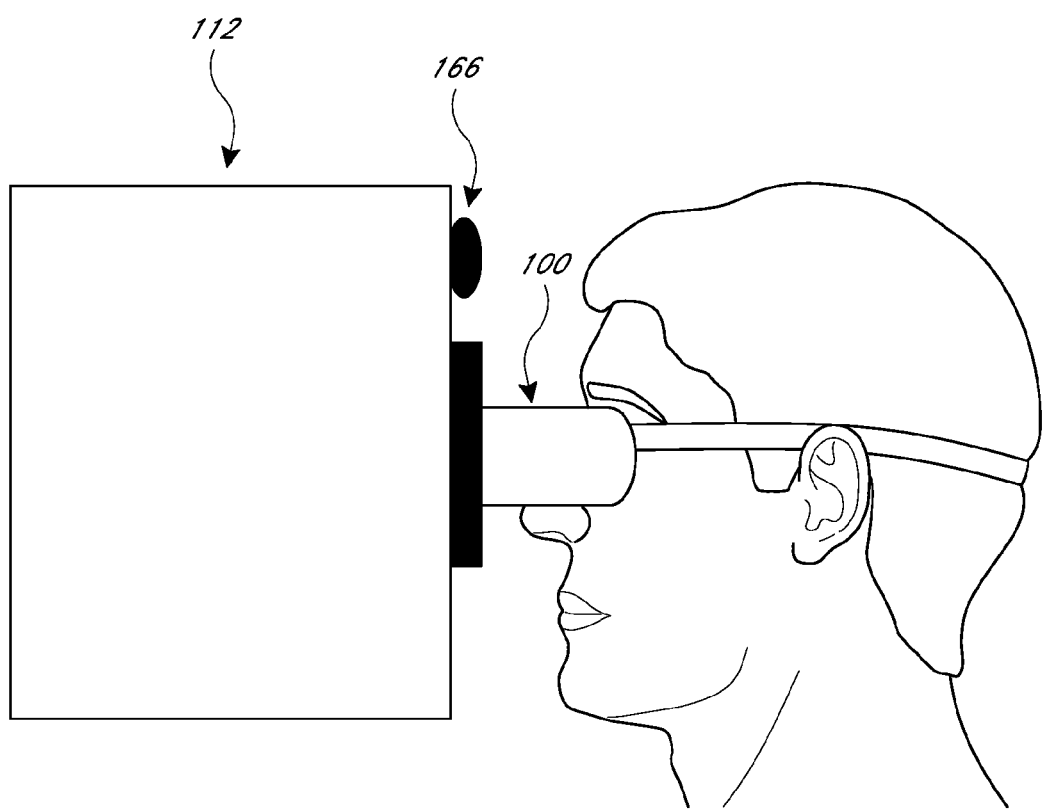
FIG. 7a schematically illustrates a side view of one embodiment of a mask displaced a first distance from a medical device.
Figure 7B:
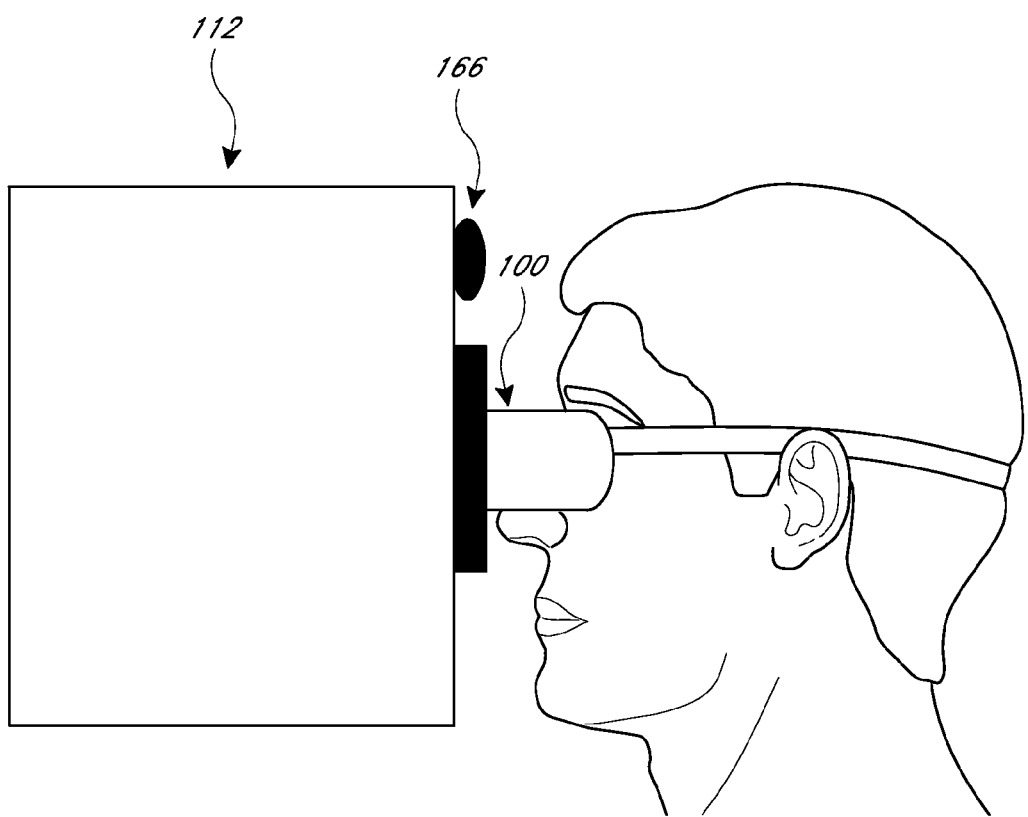
FIG. 7b schematically illustrates a side view of another embodiment of a mask displaced a second distance from the medical device.

FIGS. 7a-7b illustrate side views of a user with a mask 100 being examined or treated by a medical device 112 according to one embodiment of the invention.

It will be appreciated that the FIGS. 7a-7b are schematic drawings and may possibly exaggerate the variation in size for illustrative purposes. The medical device 112 shown in FIGS. 7a-7b can be an OCT device. Inflating the mask 100 can increase the thickness of the mask 100, so that the mask 100 can move the patient toward or away from the device 112 when it is deflated or inflated respectively. For example, FIG. 7a illustrates a relatively deflated mask 100, with a user relatively close to the device 112. FIG. 7b illustrates a relatively inflated mask 100, with the user relatively farther from the mask 100. "Inflating" or "inflated" may include a mask 100 in a fully inflated state, or a mask 100 in a less than fully inflated state, but still in a state that is more inflated relative to a previous state (e.g. a deflated state) or at least partially inflated. Similarly, "deflating" or "deflated" may include a mask 100 in a fully deflated state, or a mask 100 in a less than fully deflated state, but still in a state that is more deflated relative to a previous state (e.g. an inflated state) or at least partially deflated.

A patient location sensor 166 can be included in order to detect how close or how far the user is from the medical device 112. If the user is not at a desired distance from the device 112, the framework 154 on the mask 100 can be inflated or deflated to bring the user to the desired distance. Any variety of sensors 166 can be used to detect the distance between the user and the medical device 112, according to sensors known in the art. In one embodiment, a patient location sensor 166 can be included with the medical device 112 in alignment with the user's forehead, as illustrated in FIGS. 7a-7b. Thus, the location sensor 166 can measure, for example, the distance or relative distance from the forehead to the medical device 112. In one embodiment, the sensor 166 can be a switch, which can be actuated (e.g. activated or depressed) when the user's forehead presses against the switch when the user is close to the medical device 112. In addition, other types of sensors in different locations could measure the distance between the user and the medical device 112. In one embodiment, the location sensor 166 is not placed on the medical device 112, but is placed in a location that can still detect the distance between the user and the medical device 112 (e.g. on the walls of a room in which the medical device 112 is located). In one embodiment, the information regarding the distance between the user and the medical device 112 is provided by an OCT device.

Figure 8:
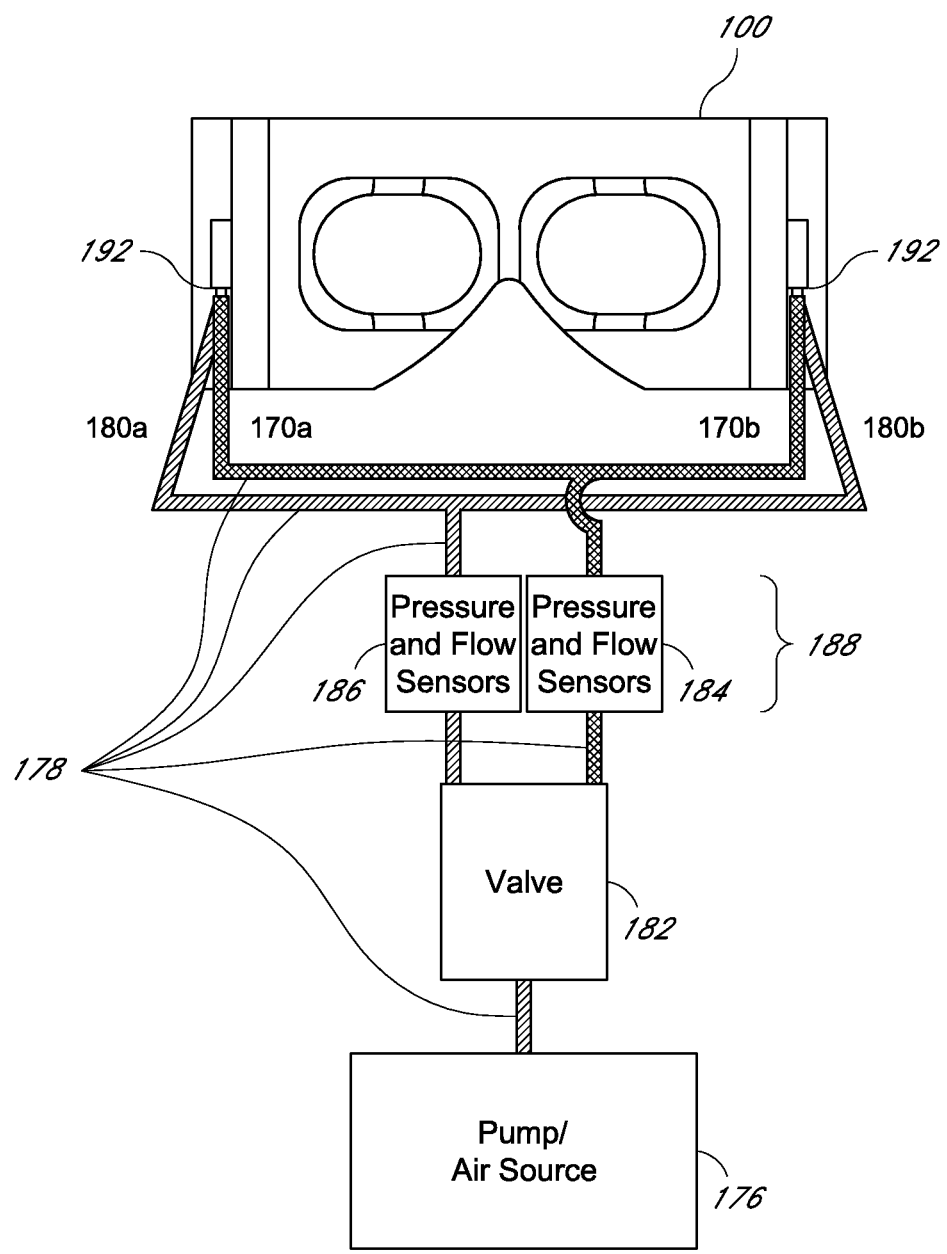
FIG. 8 schematically illustrates a schematic diagram of a system for controlling, monitoring, and providing fluid to a mask.

FIG. 8 illustrates a system 174 for controlling, monitoring, and providing air to the inflatable mask 100. The system 174 can be used to control a patient's distance from the medical device 112, the patient's movement to and from the medical device 112, the seal between the mask 100 and the patient's face, and/or pressure in the ocular cavities 160a, 160b of the mask 100.

Referring to FIG. 8, the system 174 can include pumps 176, an air source 176, conduits 178, valves 182, pressure sensors 188, flow sensors 188 and/or processors (not shown). In addition, air into and out of the inflatable chambers 150a, 150b and/or cavities 160a, 160b can be controlled by similar components. Referring to FIG. 7b, the air source/pump 176, valves 182, sensors 188, and the mask 100 can be in fluid communication with each other via conduits 178. In addition, the air source/pump 176, valves 182, and sensors 188 can be in electronic communication with a processor. Further, the processor can be in communication with electronics associated with a medical device 112, such as an OCT device.

In some embodiments, the air source/pump 176, conduits 178, valves 182, sensors 188, and processors can be contained within a single unit, such as a medical device 112. In other embodiments, the components may be spread out across several devices external to a medical device 112.

Referring to FIG. 8, the mask 100 can be connected to an air source/pump 176, which can comprise compressed air, ambient air from the environment of the mask (e.g. in a clinical room), a reservoir, a sink (e.g. for providing water to the mask 100), an automatic pump, manual pump, hand pump, dispenser, or any other suitable air source/pump.

Valves 182 can also be included in the system 174 for increasing, decreasing, stopping, starting, changing the direction, or otherwise affecting the flow of air within the system 174. In some embodiments, the valves 182 can direct air to an exhaust port, in order to vent air in the cavities 160a, 160b or inflatable chambers 150a, 150b. In some embodiments, valves 182 are not included in the ports 170a-b, 180a-b of the mask 100, and are external to the mask 100. In some embodiments, valves 182 can be included in the ports 170a-b, 180a-b of the mask 100.

In some embodiments, the system can also include an ocular pressure sensor 186 to sense the pressure inside the ocular cavities 160a, 160b. Readings from the pressure sensor 186 can be used for intraocular pressure and retropulsion measurements. In addition, the system 174 can include a chamber pressure sensor 184. In some embodiments, the chamber pressure sensor 184 can be used to determine whether a patient is pressing their face against the mask 100, or how hard the patient is pressing their face against the mask 100.

A flow sensor 188 can also be provided to measure the volume of flow into and out of the ocular cavities 160a, 160b and inflatable chambers 150a, 150b. Flow sensors 188 may be useful when, for example, the inflatable chamber 150a, 150b is under-inflated such that the pressure inside the inflatable chamber equals atmosphereic pressure. In such a case, pressure sensors 188 may not be useful but a flow sensor 188 can measure the volume of fluid pumped into the inflatable chamber 150a, 150b. In some embodiments, one set of sensors can be provided for the ocular cavities 160a, 160b, and another set of sensors can be provided for the inflatable chambers 150a, 150b.

Referring to FIG. 8, the conduits 178 can convey the flow of air (or gas, liquid, gel, etc.) between the pump/air source 176, valves 182, sensors 188, and the mask 100. In some embodiments, the valves 182 can be downstream of the pump/air source 176, the sensors 188 can be downstream of the valves 182, and the mask 100 can be downstream of the sensors 188.

In some embodiments, the conduit 178 terminates at conduit ends 192, shown in FIGS. 2a-2b. The conduit ends 192 can be designed to couple with the ports 170a-b, 180a-b of the mask 100. Referring to FIGS. 2a-b, in some embodiments, the ports 170a-b, 180a-b of the mask 100 can include a male portion (e.g. a luer lock taper connector), and the conduit ends 192 can include a female portion.

In some embodiments, the ports 170a-b, 180a-b of the mask 100 can include a female portion, and the conduit ends 192 can include a male portion. In addition, the conduit ends 192 and the ports 170a-b, 180a-b can contain flanges, tubings, or any other mechanism for coupling with each other. When the ports 170a-b, 180a-b are coupled to the conduit ends 192, an air-tight seal for fluid flow between the mask 100 and the system can be created.

Referring to FIG. 2a, in some embodiments, one movement (e.g. pressing the mask 100 down in the direction of the arrow 199) can connect all four ports 170a-b, 180a-b to the conduit ends 192 at the same time. In some embodiments, the conduit ends 192 extend to the exterior of the medical device 112, and the conduits 178 can be connected to the exterior ports 170a-b, 180a-b one at a time. In some embodiments, the conduits ends 192 are located on the medical device 112, and a separate conduit piece can connect the conduit ends 192 to the external ports 170a-b, 180a-b.

In some embodiments, the system 174 can be used in clinical settings, such as during a medical visit (e.g. a medical examination). The components can be utilized in a variety of different ways and combinations during the medical treatment.

For example, during a medical diagnostic or treatment, referring to FIG. 2a, the mask 100 can be interfaced with the medical device 112 by aligning the ports 170a-b, 180a-b of the mask 100 with the conduit ends 192 in the medical device 112, and pushing down on the mask 100.

The patient's head can be brought into contact with the rear concaved surface 122 of the mask 100, and system 174 can inflate or deflate the inflatable chambers 150a, 150b, so that the mask 100 conforms to the patient's face, thereby forming an air-tight seal around the ocular cavities 160a, 160b.

During the procedure, the system 174 can change the pressure in the air-tight ocular cavities 160a, 160b by a desired amount depending on the medical examination being taken. The pressure sensor 186 can sense the amount of pressure in the ocular cavities 160a, 160b, and send that data to the processor. In addition, the system 174 can vary the pressure in the ocular cavities 160a, 160b during the procedure. For example, the processor can increase the pump 176 speed or change the valve state 182 so that flow is restricted.

Other components in the medical device 112 can also take measurements, such as ocular measurements, which can be combined with the data sent by the pressure sensors. For example, optical imaging components can measure changes in curvature or position of the anterior of the eye and in some embodiments, compare those changes to changes in the position or curvature of posterior of the eye. In addition, changes in the locations and distances of tissues, such as in the eye, can be imaged based on the pressure in cavities 160a and 160b sensed by the pressure sensors. Thus various pieces of data can be analyzed and processed into meaningful medical information.

Further, during the procedure, the system 174 may receive data from a patient location sensor 166 (see e.g. FIG. 7a-7b) indicating the distance between the patient and the medical device 112. The processor may determine that the patient should be positioned closer to or farther away from the medical device 112, in order to obtain more accurate and precise readings. Thus, the processor may use the location of the patient to modulate the inflation or deflation of the mask 100 more or less (e.g. by changing pump speed, changing valve state, etc.), in order to bring the patient closer to or farther away from the medical device 112.

In some embodiments, the processor can switch on the pump/air source 176 and open the valves 182 to introduce air into the ocular cavities 160a, 160b or inflatable chambers 150a, 150b according to a preset pressure or flow volume goal. In addition, flow in the system can be reversed to deflate the inflatable chambers 150a, 150b.

The mask 100 may include a mechanism for easily identifying a patient according to one embodiment of the invention. For example, the mask 100 may include an RFID tag, bar code or QR code, or other physical embodiment, to identify the wearer to other devices. Thus, for example, when a patient with a certain mask 100 nears the medical device 112, the system can determine who the patient is, and execute instructions tailored for the patient (e.g. how much air is needed to properly inflate the framework 154, how much pressure should be applied to the ocular cavities 160a, 160b, what readings the medical device 112 should take, etc.)

The mask 100 can be made of a material, such as plastic (e.g. polyethylene, PVC), rubber paper, or any other suitable material. In various embodiments, the mask 100 can be configured to be disposable by making it out of inexpensive materials such as paper, rubber or plastic. In various embodiments, the mask 100 can be configured to be reusable and easily cleaned either by the wearer or by another person.

In some embodiments, the mask 100 can provide a barrier between the patient and the medical device 112, increasing cleanliness and serving hygienic purposes.

In one embodiment, the mask 100 can be configured to create a barrier to external or ambient light, such as by constructing the mask 100 out of opaque materials that block light transmission. Accordingly, the mask 100 can prevent ambient light from interfering with medical examination measurements, such as optical devices, and ensure the integrity of those measurements.

Although examples are provided with reference to "air" (e.g. introducing air into the inflatable chamber, introducing air into the ocular cavities), it will be appreciated that other substances besides air can be used, such as gas, fluids, gel, and particulate matter.

Although examples are provided with reference to a mask 100 for a binocular system, it will be appreciated that the embodiments disclosed herein can be adapted for a monoocular system. Thus, in one embodiment, the mask 100 includes an inflatable framework 154 defining one cavity instead of two, and that cavity can form a seal against the periphery of one eye socket. Further, while examples are provided with reference to eye sockets and eye examinations, it will be appreciated that the embodiments disclosed herein can be used with other tissues and medical applications.

In other embodiments, an inflatable device may cover different body tissues such as gloves for the hands, stockings for the feet or a hat for the head. In various embodiments, the inflatable device may include a cavity similar to the ocular cavity in the mask and may have at least one port to provide access to the cavity and change pressure therein or inflow gas therein or outflow gas therefrom, as well as a port to inflate the inflatable devices.

The inflatable mask can be used in a wide variety of clinical settings, including medical examinations and encounters that may be assisted by automated systems. Various embodiments of an automatic encounter portal are described below.

Electronic Encounter Portal

Medical encounters can be commonly comprised of administrative tasks, collection of examination data, analysis of exam data, and formation of an assessment and plan by the healthcare provider. In this context, a healthcare provider may be a licensed healthcare practitioner, such as a medical doctor or optometrist, allowed by law or regulation to provide healthcare services to patients. Examinations may be comprised of numerous individual tests or services that provide information for a healthcare provider to use to make a diagnosis, recommend treatment, and plan follow-up. The data from these tests that are collected for use by healthcare providers can be broken down into three rough categories: historical data, functional data and physical data.

Historical data can be collected in many ways including as a verbal person-to-person interview, a written questionnaire read and answered by the patient, or a set of questions posed by an electronic device either verbally or visually. Typical categories of historical information that are obtained in medical exams can include but are not limited to a chief complaint, history of present illness, past medical history, past ocular history, medications, allergies, social history, occupational history, family history, sexual history and a review of systems.

Functional data can be collected through individual tests of function and can be documented with numbers, symbols or categorical labels. Examples of general medical functions can include but are not limited to measurements of blood pressure, pulse, respiratory rate, cognitive ability, gait and coordination. Ophthalmic functions that may be tested during an exam can include but are not limited to measurements of vision, refractive error, intraocular pressure, pupillary reactions, visual fields, ocular motility and alignment, ocular sensation, distortion testing, reading speed, contrast sensitivity, stereoacuity, and foveal suppression.

Physical data can capture the physical states of body tissues and can be collected in many forms, including imaging, descriptions or drawings, or other physical measurements. This may be accomplished with simple measurement tools such as rulers and scales. It may also be accomplished with imaging devices, such as color photography, computed tomography, magnetic resonance imaging, and optical coherence tomography (OCT). Other means to measure physical states are possible. Physical measurements in general medical exams can include height, weight, waist circumference, hair color, and organ size. Ophthalmic structural measurements can include but are not limited to slit lamp biomicroscopy, retinal OCT, exophthalmometry, biometry, and ultrasound.

Currently, almost all of the individual tests that make up a medical examination are conducted by a human laborer often through the operation of a device. Whether this person is a healthcare provider or an allied healthcare professional, these laborers can be expensive, can often produce subjective results, and can have limitations on their working capacity and efficiency. Given the labor intensive nature of exams, healthcare care practices (which may also be referred to herein as "clinics" or "offices") and in particular eye care practices often employ numerous ancillary staff members for every healthcare provider and dedicate large areas of office space for waiting rooms, diagnostic equipment rooms and exam rooms. All combined, these overhead costs make healthcare expensive, inefficient and often prone to errors.

Automation is a well-known way of improving efficiency and capacity as well as reducing unit costs. Patient-operated or entirely operator-less devices may be preferable as labor costs increase and the need for objective, reproducible, digital, quantitative data increases.

Figure 9:
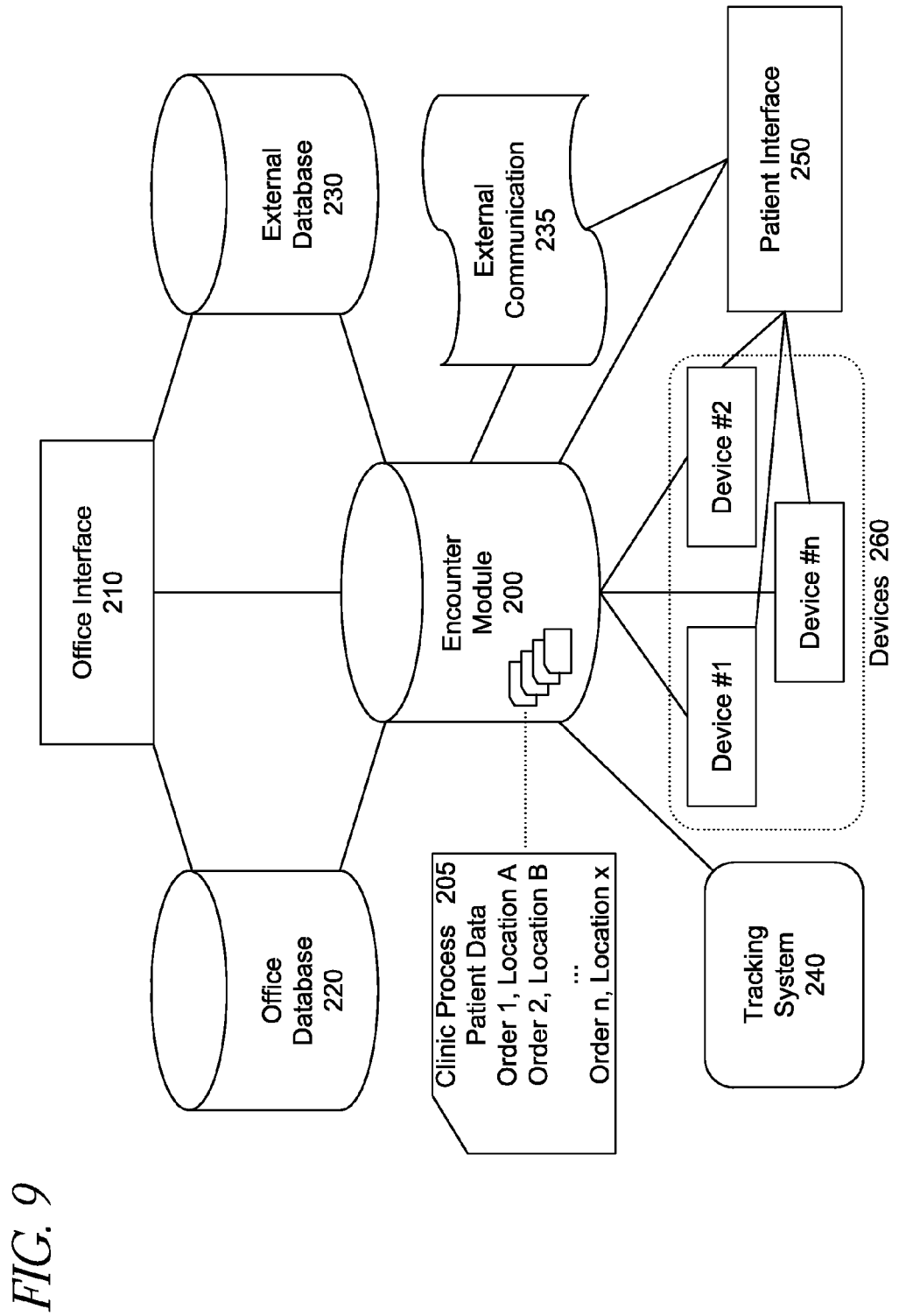
FIG. 9 schematically illustrates a schematic diagram an electronic exam portal.

With reference to FIG. 9, there is illustrated one embodiment of an electronic encounter portal. The encounter module 200 can be an electronic device that may be comprised of, for example, data storage, communication, or computer code execution capabilities and may contain information on patients registered for a healthcare encounter in an office.

The office interface 210 can be comprised of software that may be used by people to interact with the encounter module 200. Other software may also be included in the office interface 210. In one embodiment, the office interface 210 also can be comprised of an electronic device, such as a computer, tablet device or smartphone. In various embodiments, office staff can use the office interface 210 to, for example, create records or enter patient data into the encounter module 200 for patients who register in the clinic. This data entry can be enabled in many ways, including for example, manual entry, entry by copying previously-entered data from an office database 220, or entry using a unique identifier that can be compared to an office database 220 or external database 230, such as an Internet or cloud-based database, to retrieve pre-entered data for a patient matching that unique identifier. In one embodiment, registration can be completed with a code, such as an encounter code, in a fashion similar to checking in for an airline flight at an airport. This code could, for example, by linked to patient or provider information required for registration purposes.

The office database 220 can be configured to store data from past encounters, as well as other types of data. The external database 230 can be also configured to store at least data from past encounters, as well as other types of data. The encounter module 200 can be configured, for example, to access, copy, modify, delete and add information, such as patient data, to and from the office database 220 and external database 230. The external database 230 can be configured to, for example, receive, store, retrieve and modify encounter information from other offices.

In one embodiment, patients may self-register or check into the clinic by using the office interface 210 to, for example, create an encounter record, enter encounter information manually, select their information from a pre-populated office database 220, or enter a unique identifier that can be compared to an office 220 or external database 230 to retrieve their other associated data.

The encounter module 200 can be configured to contain patient records which may also contain clinic processes 205. A clinic process 205 can be comprised of, for example, orders from the healthcare provider for the patient's care. In one embodiment, the orders may indicate the sequence of evaluations and care. For example, a provider may indicate that a given patient should undergo a medical history followed by an examination with various medical devices followed by an assessment by the provider.

In one embodiment, the clinic process 205 can be configured to enable alteration of the orders, the order sequence or both the orders and their sequence by, for example, office staff or the provider. Examples of this could include insertion of an educational session about a given disease prior to a discussion with the provider, deletion of a treatment denied by a patient, or switching the sequence of two test procedures.

In some embodiments, the prescribed orders themselves may contain lists of prescribed tests to be performed on a given device. For example, as part of a technician work-up order, a provider may prescribe blood pressure and pulse measurement testing to be performed on a patient using a device in the clinic. The order and prescription of these tests may change throughout the encounter having been altered by office staff, the provider, or electronic devices.

In one embodiment, a diagnosis or medical history of a patient from the encounter module 200 can be included in the clinic process 205 and may be used, for example, to determine or alter the clinic process 205. For example, a history of past visits and evaluations may alter the tests that are ordered or the devices that are used during an encounter.

In one embodiment of an electronic encounter portal, a tracking system 240 can be configured to enable a component of an electronic encounter system to determine the physical location or position of, for example, patients, providers and staff in the office space. In one embodiment, a component of the electronic encounter system can use data from the tracking system 240 to monitor the progress of patients through a clinic process 205. In one embodiment, this tracking system 240 can be comprised of a sensing technology, such as a compass, radiofrequency antenna, acoustic sensor, imaging sensor, or GPS sensor that determines the position of the sensor in relation to known objects such as office walls, positioning beacons, WiFi transmitters, GPS satellites, magnetic fields or personnel outfitted with radiofrequency ID tags.

The tracking system 240 may also be configured to perform mathematical calculations, such as triangulation, to analyze signals from the sensors. The tracking system may also compare signals from the sensors to databases of known signals collected at a prior date, such as comparing a measured magnetic field to a database of known magnetic fields at every position in the clinic. In some embodiments, this tracking system 240 can also be comprised of an emission technology such as a radiofrequency beacon, to indicate the position of an object in the office space.

The tracking system 240 may also be configured to localize the position of a person or object using a known map of the office space as shown in FIG. 3. Knowledge of the position of sensors, patients or personnel in an office space map may enable the tracking system 240 to provide information to the encounter module 200 regarding the location of patients, providers or other office personnel in an office space.

The tracking system 240 can also be configured to provide position information to other components of the electronic encounter system, such as the office interface 210 or the patient interface 250, either directly or via an intermediate component such as the encounter module 200. An example of how this information might be used is to provide status information to a user as to the progress or status of other people in the office.

In one embodiment, office personnel can use the office interface 210 to monitor the location or progress of, for example, providers, staff or patients within the office space. This monitoring may include calculation of, for example, time spent in a given location, progress through a clinic process 205, or current status of activity, such as waiting, working or occupied. This monitoring ability can be advantageous so that office staff can, for example, monitor delays in the provision of patient care or identify recurrent patient flow bottlenecks that can be reduced through optimization of clinic flow.

The patient interface 250 can be comprised of software that may be used by patients to interact with the encounter module 200. In one embodiment, the patient interface 210 can also comprise an electronic device, such as a computer, tablet device or smartphone which can be supplied by the clinic or be supplied by the patient. For the purpose of clarity, in one embodiment, the patient interface 250 may be the patient's own electronic device, such as a smartphone or computer, that can be configured with patient interface 250 software. In other embodiments, the office interface 210 and the patient interface 250 may be the same device, such as with a mobile tablet computer or smartphone, that can be configured to allow a patient to perform actions of both an office interface 210, such as registration, and actions of a patient interface 250, such as viewing patient data or asking electronic questions of office personnel.

The encounter module 200 and the patient interface 250 can be configured to interface with various devices 260 in the clinic. These devices 260 can include but are not limited to diagnostic instruments, such as blood pressure monitors, imaging devices or other measurement instruments, or therapeutic devices, such as lasers or injection apparatuses. The encounter module and the patient interface 250 can be configured to send and receive data with these devices 260. Communication with these devices 260 can be enabled by but is not limited to wired connections, wireless connections and printed methods, such as bar codes or QR codes.

With reference to FIG. 3, there is illustrated a map of a healthcare office. In one embodiment, the patient can register for a healthcare encounter at the office entrance 300. In other embodiments, the patient may register for a healthcare encounter at a place other than entrance 300. In one embodiment, encounter registration can be completed by a human receptionist who may enter information into the encounter module 200 through the office interface 210. In another embodiment, registration may be completed by the patient for example by using an assisted or self-service kiosk configured with an office interface 210.

A kiosk may, for example, be comprised of a location where an untrained user can perform a task or tasks, such as checking in for an appointment or performing a requested test. This kiosk may be comprised of electronics or computer equipment, may be shielded from the view of other people in the same room, may be comprised of seating, and may provide a material result to a user. Other kiosk configurations are possible.

In another embodiment, the patient may register for the encounter with an office interface 210, such as a tablet computer, that is supplied by the clinic and may have been configured with software to interface with the encounter module 200. In still another embodiment, the user may register for the encounter with their own portable device, such as a mobile phone or tablet computer, that can be configured with software that can allow it to act as either or both an office interface 210 or as a patient interface 250.

In various embodiments, orders or steps in an electronic encounter system can include, for example, asking a patient to sit in waiting area 310, asking a patient to proceed to testing area 320 or asking a patient to go to clinic area 330. These orders can be conveyed to the patient by, for example, the patient interface 250 or by office personnel. In one embodiment, the desired disposition for a patient can be determined by a clinic process 205 that may have been entered into the encounter module 200 and communicated to the patient via the patient interface 250 or office personnel.

In one embodiment, the patient interface 250 can be configured to use information from the tracking system 240 for example, to determine the location of the patient in the clinic, to determine the next planned location for a patient from a clinic process 205 in the encounter module 200, or to communicate directions to a patient using the patient interface 250.

Figure 10:
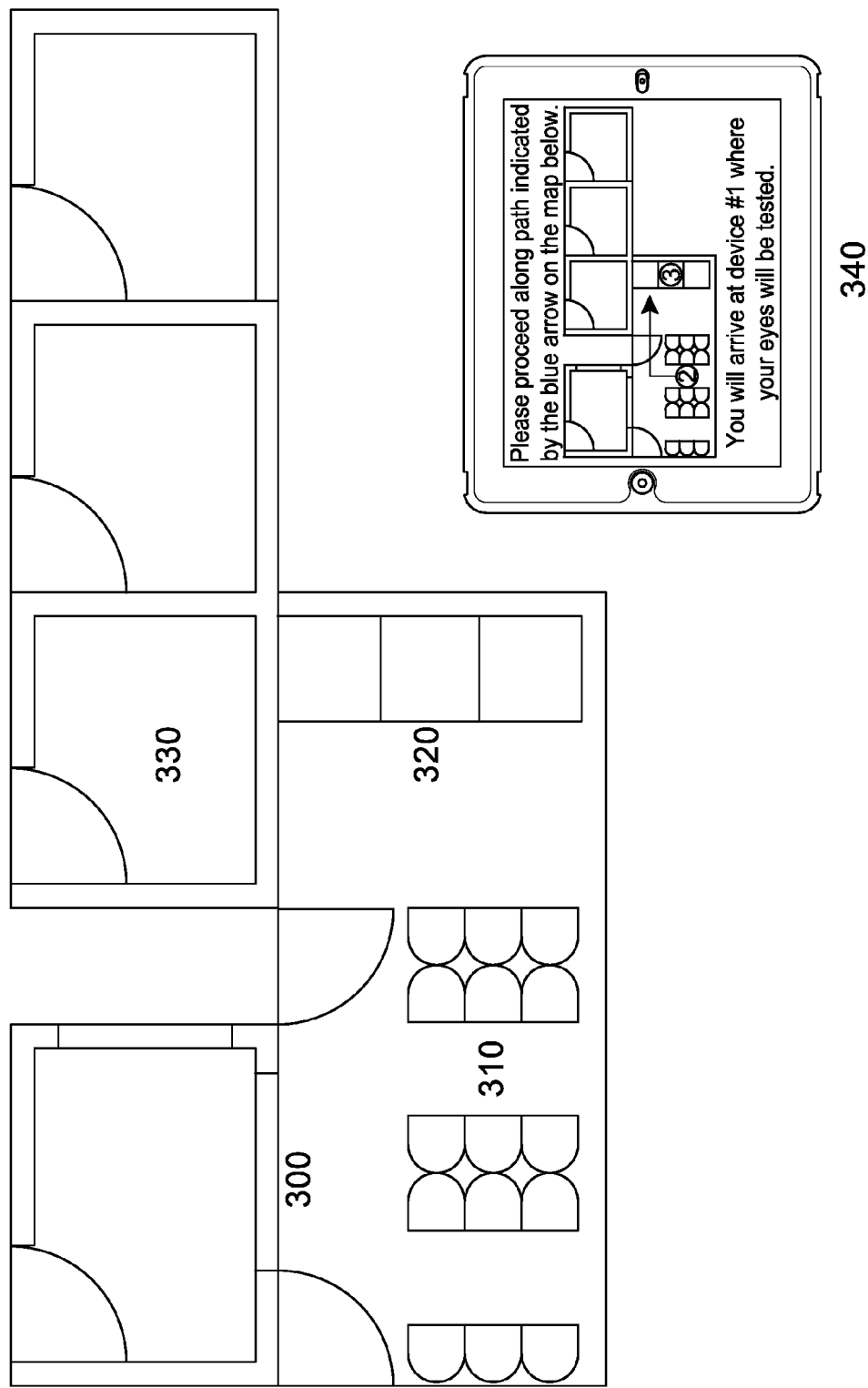
FIG. 10 schematically illustrates a healthcare office map.

Referring to FIG. 10, in one embodiment 340, a line can be drawn on a schematic map of the clinic space on patient interface 250 to show the patient how to walk to their next destination in the clinic. In another embodiment, the patient interface 250 can be configured to communicate directions verbally, such as by text-to-speech software.

In one embodiment, the encounter module 200 may be configured to monitor which rooms and devices in an office are "in use" based on information provided by the tracking system 240. In one embodiment, the encounter module 200 may be configured to select a next location for a patient based on which rooms or devices 260 may be free to use. For example, if the encounter module 200 determines that a device 260 required for the next stage of a clinic process 205 is occupied or busy, the encounter module 200 can be configured to alter the clinic process 205 by inserting, for example, a waiting room order that, for example, can be removed from the clinic process 205 when the required device is free for use.

In one embodiment, the encounter module 200 can be configured to monitor utilization of a device 260 or clinic area that may be required for the next stage of a clinic process 205 and may be configured to insert an order for a patient to move to that device 260 or clinic area when it becomes free for use.

In another embodiment, the encounter module 200 can be configured to monitor the list of patients waiting for a provider and also to determine which providers have the shortest waiting lists or waiting times based on, for example, the number of patients in a waiting patient list and the average time the provider spends with each patient. The encounter module 200 can be configured to use this information, for example, to assign patients to providers with the shortest wait times so as to improve clinic flow. Numerous other embodiments of device decisions based on dynamic knowledge of device and space utilization within an office space are possible.

Figure 11:
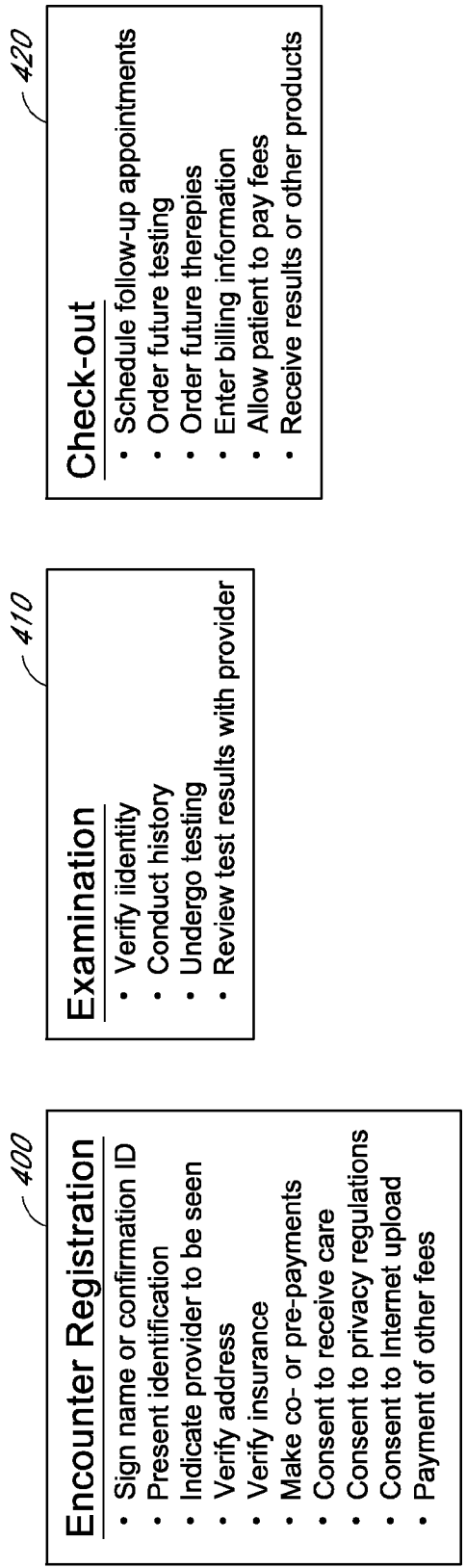
FIG. 11 schematically illustrates a block diagram of a sample healthcare encounter.

An example of a healthcare encounter is shown in FIG. 11. In one embodiment, the first step in the encounter may be registration 400 which can be completed, for example, by office staff or by the patient using, for example, an office interface 210. Encounter registration 400 may be comprised of many steps such as signing the patient's name and address, presenting identification, verifying insurance status, paying co-payments due prior to the encounter, consenting to be seen by the provider, consent to privacy regulations or payment of other fees. In other embodiments, the user may skip registration 400 and may proceed to other steps, such as examination 410.

In one embodiment, one step in an automated healthcare encounter can be verification of the user's identity. This may be accomplished, for example, as part of registration 400, as part of examination 410, prior to using any device 260, or at other times in the encounter. A mobile patient interface 250 may be advantageous since it can verify the user's identity once and then communicate this identity to, for example, the encounter module 200, to providers, or to subsequent devices used throughout the encounter, such as devices 260.

In various embodiments, the patient interface 250 can be configured to verify the user's identity through biometrics, such as through recognition of the patient's face, voice, fingerprint or other unique physical aspects of the subject. In other embodiments, the patient interface 250 can be configured to verify the user's identity through confirmation of a user's unique data, such as their names, date of birth, addresses, mother's maiden name, or answers to questions only known to the user. In another embodiment, the patient interface 250 can be configured to verify the user's identity through confirmation of code, such as a password or secret code known only to the user. In still another embodiment, the patient interface 250 can be configured to verify the user's identity through coupling of a device carried only by the user, such as a key, electronic device, bar code or QR code.

In one embodiment of an electronic healthcare encounter, the user may complete the history portion of their examination as part of their overall encounter. As discussed previously, in various embodiments, the history portion of the encounter can be collected, for example, by office staff or by the patient themselves. Office staff may use the patient interface 250 or the office interface 210 to conduct or enter results from a patient history. In other embodiments, the patient may use the patient interface 250 to complete their own history without interacting with office staff.

In various embodiments, the questions can be configured in a form that facilitates responses using written, mouse-based, tablet-based or voice entry such as multiple choice, true or false, or pull-down menu selections. In other embodiments, the questions may require free entry such as by writing, voice dictation, or keyboard entry. In these examples, the patient interface 250, the office interface 210 or the encounter module 200 may be configured to interpret electronic forms of these inputs, such as electronic writing or voice dictation.

In one embodiment, the history portion of the encounter may be comprised of a standard series of questions. In another embodiment, the series of questions may be based on, for example, a preference specified by the provider, the patient's diagnosis, the patient's symptoms or some other unique aspect of the encounter.

In still another embodiment, the history portion of the encounter can be comprised of questions from a database whereby the next question to be asked can be determined, for example, based on an answer to a previous question. This dynamically-traversed database of questions may use answers from a question to determine subsequent questions to ask or to determine sets of questions to ask based on a tree organization of questions in the database. For example, if a patient reports color vision loss, the system can be configured to add a series of questions related to color vision loss to its list of questions even if they were not previously included in the set of questions to be asked. In later questioning, it the patient reports pain on eye movement, the system can be configured to add, for example, questions related only to pain on eye movement or questions related to pain on eye movement and color vision loss. The dynamic allocation of new questions based on answers to previous questions can be configured such that a provider can allow or disallow such a feature.

In one embodiment, a dynamically-traversed electronic questionnaire can be configured to assign priority values to each question so that certain questions can be asked before other questions. In still another embodiment, the system can provide a running count of the total number of questions to be asked to the patient along with an estimated total time to completion. In related embodiments, the system can be configured to allow users or providers to shorten the questionnaire, such as by excluding lower priority questions, based on aspects of the dynamic questionnaire such as it taking too much time or involving too many questions and answers.

In another embodiment, the patient interface 250 can be configured to allow the user to change display parameters, such as size, color and font type, used to display questions with the patient interface 250. In other embodiments, the patient interface 250 can be configured to read questions aloud, for example using a text-to-speech system or pre-recorded voices, or to ensure privacy by providing a headphone jack where the user can connect headphones.

In one embodiment, the encounter module 200 can be configured to direct devices 260 to perform tests and store results associated with the clinic process 205 and the patient's information contained within the encounter module 200. The encounter module 200 can be configured to communicate with these devices 260 using a direct wired connection, such as a USB, Ethernet or serial connection, a wireless connection, such as Bluetooth® or 802.11, an intermediate electronic device, such as a USB key, memory card or patient interface 250, or a physical coded embodiment such as a bar code or QR code.

In one embodiment, the encounter module 200 or patient interface 250 can be configured to alter the list of tests requested for an encounter based on answers to history questions or results from testing on devices 260. The encounter module 200 or the patient interface 250 can also be configured to direct a device 260 to conduct a new test or tests in addition to or in place of the old test or tests. Alteration of the clinic process 205 by the encounter module 200 or patient interface 250 can be allowed or disallowed by a provider either globally or specifically, such as based on answers to specific questions or categories of questions, using, for example, the office interface 210.

In one embodiment, the encounter module 200 or the patient interface 250 can be configured to initiate operation of a device 260, such as an instrument to measure vision. In another embodiment, the encounter module 200 or the patient interface 250 can be configured to allow the user to initiate operation of a device 260, such as by saying "ready", pushing a button or pressing a pedal that may be attached to the patient interface 250. In still another embodiment, the encounter module 200 or the patient interface can be configured to allow the user to initiate operation of the device 260, such as by saying "ready", pushing a button or pressing a pedal, through the device 260.

As discussed previously, the encounter module 200 or the patient interface 250 can be configured to receive data, such as examination results, from devices, such as the tracking system 240, the patient interface 250 or devices 260. As discussed above, the encounter module 200 can be configured to communicate with these other components using, for example, a wired connection, a wireless connection, an intermediate electronic, or using a physical embodiment.

Collection of data from numerous devices by the patient interface 250 or encounter module 200 can be particularly advantageous by reducing transcription or sorting errors that can occur when human laborers are involved in these processes or by centralizing all encounter data in one location.

Various components in the electronic encounter system, such as the encounter module 200, can be configured to compile encounter data into a digital package or packages that can be uploaded to, for example, an electronic health record system either in the office, such as the office database 220, or outside the office via secure external communication 235, transmitted to other individuals on a patient's healthcare team via secure external communication 235, reviewed directly by the provider on a patient interface 250 or office interface 210, or stored on an accessible external database 230. The external database 230 can be configured to be accessible remotely, such as via the Internet, for example, to facilitate sharing of exam data between providers or to facilitate access by the patient to their own healthcare data.

As discussed previously, the encounter module 200 can be configured to track both patients and clinic personnel using the tracking system 240. The encounter module 200 can be configured to store tracking information such that it, for example, can be viewed or analyzed using an office interface 210. By tracking a patient's location over time, the encounter module 200 can be configured to develop clinic patient flow maps that may enable staff to identify both acute and chronic problems with clinic flow. For instance, identification of a patient by the encounter module 200 who has been waiting longer than a pre-defined threshold value stored in a clinic process 205 can alert the staff, for example via an office interface 210, to address problems with that patient's encounter that might be leading to this delay. Identification of chronic bottlenecks and waiting points across numerous encounters can allow practices to optimize their workflow.

Providers can be tracked in several ways. In one embodiment, mobile office interfaces 210 can be configured with tracking systems 240 to identify the location and identity of providers carrying them. In another embodiment, the patient interface 250 can be configured to require providers to log in whenever they are consulting with a patient. In still another embodiment, the tracking system 240 can be configured to monitor the location or identity of providers wearing identifiers, such as RFID tags. In other embodiments, the encounter module 200 could be configured to communicate updates to patients, such as by using the patient interface 250, to, for example, estimate the approximate wait times until the provider sees them or to convey how many patients still need to be seen by the provider before they are seen by the provider.

The electronic encounter portal can also be configured to provide entertainment or education to a patient. For example, the patient interface 250 can be configured to provide Internet access 235, access to previous encounter records stored on the encounter module 200, or access to previous encounter records stored on the external database 230. The patient interface 250 can also be configured to provide access by the patient to educational resources, potentially targeted toward the diagnosis or future treatments for a patient, that may be stored on components such as the encounter module 200. In one embodiment, the provider can use a patient interface 250 or an office interface 210 to enter orders for an educational program into a clinic process 205.

In another embodiment, the patient interface 250 can be used to inform a patient about clinic resources, such as clinical trials, support programs, therapeutic services, restrooms, refreshments, etc. based on information stored on the encounter module 200. The encounter module 200 can also be configured to direct patients to these resources, such as restrooms, based on information from the tracking system 240 and requests from the patients using the patient interface 250. The encounter module 200 can also be configured to manage communications between patients, using a patient interface 250 and office staff, such as by using an office interface 210.

In one embodiment, the patient interface 250 can be configured to store data from devices and, in an embodiment that is mobile such as a tablet or smartphone, can allow the patient to transport encounter data through the clinic process 205 for review by or with the provider. In another embodiment, the office interface 210 can be configured to enable data to be uploaded for review by the provider. Both the patient interface 250 and the office interface 210 can be configured to access and use prior visit data from the encounter module 200 to enhance assessments of a patient's healthcare status. Similarly, both the patient interface 250 and the office interface 210 can be configured to access prior data from the external database 230 to enhance assessments of a patient's healthcare status.

In related embodiments, the encounter module 200 and the external database 230 can be configured to act as common locations for encounter data that can be accessed by both patients and providers. The external database 230 can be configured to allow remote access to encounter data by both providers and patients when they are outside of the office. Similarly, the external database 230 can be configured to receive data from devices 260 at locations outside of the described office and share these results with the encounter module 200 for example, to enable automated remote healthcare encounters.

In one embodiment of an electronic encounter portal, a check-out procedure 420 may be the last order or step in a clinic process 205. In various embodiments, the office interface 210 or the patient interface 250 can be configured to allow providers to enter orders for future encounters such as testing or therapies. In other embodiments, the office interface 210 can be configured to enable the provider to enter billing information to be submitted for insurance reimbursement or directly charged to the patient. In still another embodiment, the office interface 210 can be configured to allow the provider to recommend a follow-up interval for the next encounter. In a related embodiment, the office interface 210 or the patient interface 250 can be configured to allow the patient to select the best time and data for a follow-up encounter. In another embodiment, the office interface 210 can be configured to allow the provider to order educational materials or educational sessions for the patient that may occur after the encounter concludes.

Accordingly, various embodiments described herein can reduce the need for clinic personnel to perform these tasks. In addition, various embodiments enable users to conduct their own complete eye exams.

Automated Eye Examination

Figure 12:
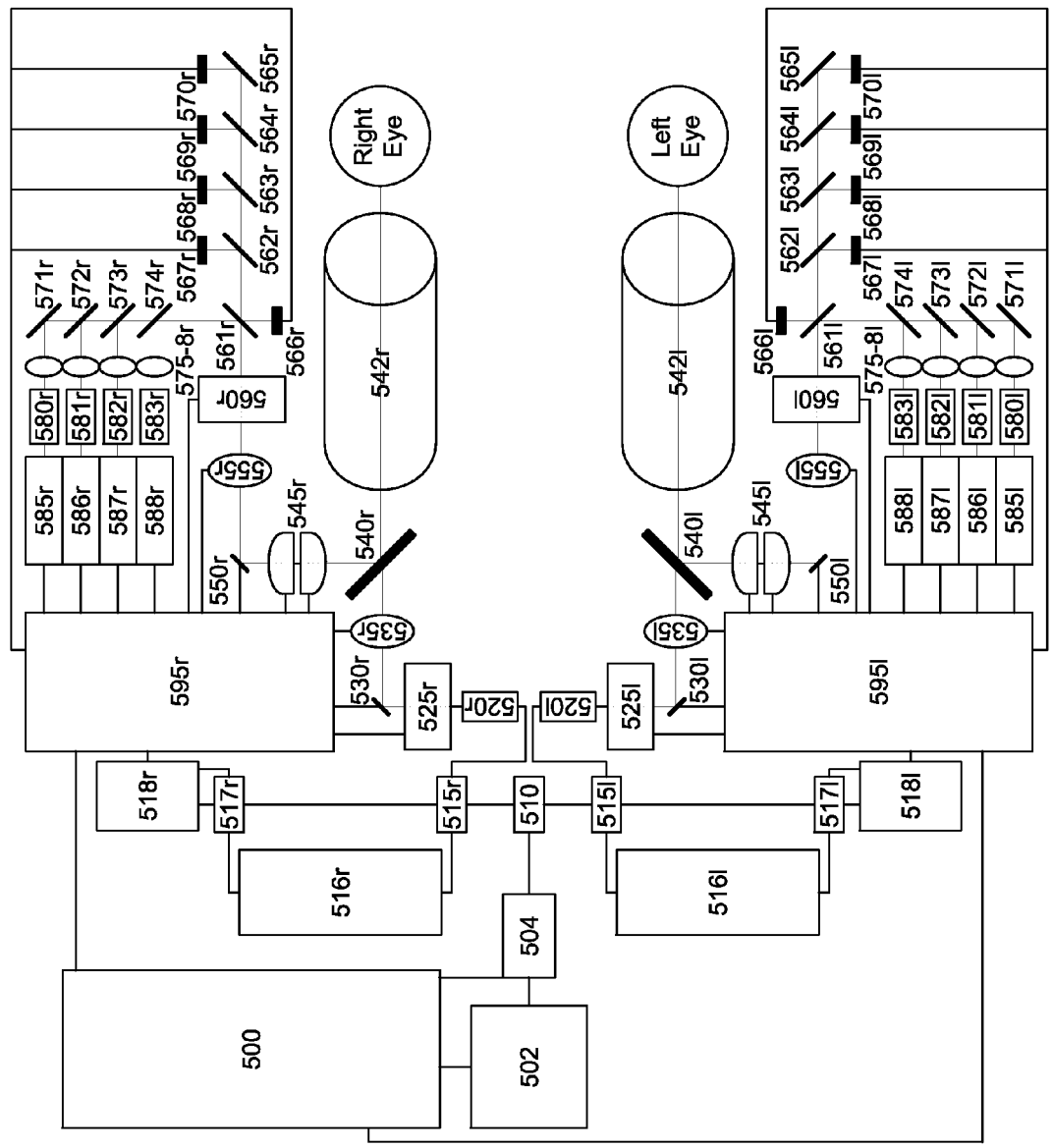
FIG. 12 schematically illustrates a binocular eye examination system based on optical coherence tomography.

FIG. 12 shows an example of a binocular eye examination system based on optical coherence tomography. Component 500 may be comprised of the main electronics, processors, and logic circuits responsible for control, calculations, and decisions for this optical coherence tomography system. Light can be output from light source 502 which may be controlled at least in part by component 500. The light source may be comprised of a broadband light source such as a superluminescent diode or tunable laser system. The center wavelength for light source 502 can be suitable for optical coherence tomography of the eye, such as 840 nm, 1060 nm, or 1310 nm. The light source 502 may be electronically controlled so that it can be turned on, off or variably attenuated at various frequencies, such as 1 Hz, 100 Hz, 1 kHz, 10 kHz or 100 kHz. In one embodiment, light from light source 502 can travel through interferometer 504, which may be comprised of a Mach Zender or other type of interferometer, where a k-clock signal can be generated. This electronic signal can be transmitted to electronics on component 500 or other components in the system and can be captured on a data acquisition system or used as a trigger for data capture.

The k-clock signal can be used as a trigger signal for capturing data from balanced detectors 518$r$ and 518$l$. Alternatively, the k-clock signal can be captured as a data channel and processed into a signal suitable for OCT data capture. This k-clock signal can be captured all of the time, nearly all of the time or at discrete times after which it would be stored and recalled for use in OCT capture. In some embodiments, various parameters of the k-clock signal, such as frequency or voltage, can be modified electronically, such as doubled or quadrupled, to enable deeper imaging in eye tissues. In various embodiments with light sources that sweep in a substantially linear fashion, the k-clock can be removed and a regular trigger signal may be employed. In various embodiments, the trigger signals used by electronics 595$r$ and 595$l$ may be synchronized with other components of the system, such as mirrors, variable focus lenses, air pumps and valves, pressure sensors and flow sensors.

Most of the light, such as 90% or 95%, that enters the interferometer 504 can be transmitted through interferometer 504 to a beam splitter or coupler 510. As used herein, "coupler" may include splitters as well as couplers. Beam coupler 510 can split the light from interferometer 504 or light source 502 to two output optical paths, specifically right and left, that lead directly to couplers 515$r$ and 515$l$. Henceforth, designation of a device or component with a suffix of 'r' or 'l' will refer to two devices that may be of the same type but are located in different optical paths. For example, one component may be located in the optical path of the right eye, designated as 'r,' and the other is located in the optical path of the left eye, designated as 'l.'

The optical paths in this system may be comprised of fiber optics, free space optics, a mixture of free space and fiber optics. Other combinations are also possible. The split ratio of coupler 510 can be a predefined ratio, such as 50/50 or 70/30. Light from coupler 510 can travel to couplers 515r and 515l. Couplers 515r and 515l may also split light from coupler 510 with a predefined split ratio such as a 50/50, 70/30, or 90/10. The split ratios for couplers 510, 515r and 515l may be the same or different split ratios.

One portion of light from couplers 515r and 515l, such as 70%, can travel to a so-called 'reference arm' for each of the right and left optical paths. The reference arm of a light path is distinguished from the so-called sample arm of the light path since light in the reference arm of the system does not interface with eye tissue directly whereas light in the sample arm is intended to contact eye tissue directly.

The main component in the reference arm may be an optical delay device, labeled as 516r and 516l in the right and left optical paths of the system. Optical delay devices can introduce a delay, such as 1 picosecond, 10 picoseconds or 100 picoseconds, into a light path to enable matching of the overall path length of one optical path to the optical path length of another light path. In various embodiments, this optical delay may be adjustable, such as with an adjustable free light path between two collimating optical devices, a fiber stretcher that increases or decreases the length of a fiber optic, or a fiber Bragg grating that delays light based on changes in the angle of incidence of light.

In other embodiments, this optical delay line can include variable attenuators to decrease or increase the transmission of light, optical switches or mechanical shutters to turn the light off or on. Although pictured in the reference arm of this system, an optical delay line can also be entirely included in the sample arm optical path for each eye or contained in both the reference and sample arm light paths. Other combinations of sample and reference light paths are also possible.

In one embodiment, light from optical delay devices 516r and 516l can travel to couplers 517r and 517l where it may be combined with light from the sample arm that has been transmitted from couplers 515r and 515l. Couplers 517r and 517l may combine light from two light paths with a predefined ratio between paths such as a 50/50, 70/30, or 90/10. Light from couplers 517r and 517l may travel through two outputs from couplers 517r and 517l to balanced detectors 518r and 518l where the light signal can be transformed into an electrical signal, for example through the use of photodiodes configured to detect the light input from couplers 517r and 517l.

The electrical signal generated by balanced detectors 518r and 518l can be in various ranges, including but not limited to −400 mV to +400 mV, −1V to +1V, −4V to +4V and have various bandwidths, including but not limited to 70 MHz, 250 MHz, 1.5 GHz. The electrical signal from balanced detectors 518r and 518l may travel via an electrical connection, such as a coaxial cable, to electronics 595r and 595l where it can be captured by a data acquisition system configured to capture data from balanced detector devices. Although not pictured here, a polarization sensitive optical component can be disposed before balanced detectors 518r and 518l to split two polarities of light in a single light path into two optical paths. In this embodiment, two optical paths leading to balanced detectors 517r and 517l would be split into a total of four optical paths which would lead to two balanced detectors on each side.

One portion of light from couplers 515r and 515l, such as 30% or 50%, can travel to a so-called sample arm of each of the right and left optical paths. In various embodiments, the system may be configured to transmit the light through fiber optic cable or through free space optics. Light from couplers 515r and 515l can travel to optics 520r and 520l which may be collimators configured to collimate the light from couplers 515r and 515l. Light from optics 520r and 520l can travel to lens systems 525r and 525l which may be comprised of fixed focus or variable focus lenses.

In various embodiments, these lenses can be fabricated from plastic or glass. In other embodiments, these lenses may be electrowetting lenses or shape-changing lenses, such as fluid-filled lenses, that can vary their focal distance based on internal or external control mechanisms. In one embodiment, variable focus lenses in lens systems 525r or 525l may have their focal length modified by electrical current or voltage applied to lens systems 525r or 525l. This control may come from electrical components 595r and 595l and the parameters of this control may be based on pre-determined values or may be derived during operation of the system based on input received from other components of the system.

The lenses in lens systems 525r and 525l can be configured to have anti-reflective coatings, embedded temperature sensors, or other associated circuitry. Lens systems 525r and 525l may be comprised of a single lens or multiple lenses. The lenses comprising systems 525r and 525l may be present at all times or may be mechanically moved in and out of the light path such as by an attached motor and drive circuit under electrical control from components 595r and 595l. Configuration of lens systems 525r and 525l to be moveable can enable imaging at different depths in an eye tissue by introducing and removing vergence in the optical system.

Light from lens systems 525r and 525l can travel to movable mirrors 530r and 530l. Movable mirrors 530r and 530l may be comprised of MEMS (microelectromechanical systems) mirrors, controlled by galvanometers, or moved by other means. Movable mirrors 530r and 530l can be comprised of a single mirror that reflects light across 2 axes, such as X and Y, can be comprised of a single mirror that reflects light across one axis only, or can be comprised of two mirrors that each reflect light across one axis only said axes being substantially perpendicular to each other.

Electrical control of mirrors 530r and 530l, which may control each axis of reflection independently, can be provided by components 595r and 595l. The electronic control of mirrors 530r and 530l may be configured to enable variable amplitude deflections of mirrors 530r and 530l. For example, for a given drive frequency in a given axis, the current or voltage applied to mirrors 530r and 530l may enable larger or smaller amplitude deflections of the mirror surface, thus creating a zoom effect where the created image can be made smaller or larger.

Light that has been reflected from movable mirrors 530r and 530l can travel to lens systems 535r and 535l. Lens systems 535r and 535l may be fixed or variable focus lenses that are located in the optical light path at all times or only part of the time. Electrical control of lenses 535r and 535l, can be conducted by components 595r and 595l and may include for example moving these lenses in and out of the light path or changing their focal lengths. Other actions are also possible.

Light from lens systems 535r and 535l can travel to optics 540r and 540l which may be comprised of dichroic mirrors or couplers. Optics 540r and 540l may be configured to transmit light from lens systems 535r and 535l and combine it with light from lens systems 545r and 545l. Light from optics 540r and 540l can travel to eye pieces 542r and 542l before being transmitted to the right and left eye tissues.

Eye pieces 542r and 542l can be configured as multi-element lens systems such as Ploessel-type eyepieces, Erfle-type eyepieces, telescopes or other designs. In some embodiments, optics 540r and 540l may be configured to be part of or inside of eyepieces 542r and 542l. In other embodiments, variable focus lenses or polarization-sensitive optics and beam splitters can be configured inside eyepieces 542r and 542l to enable wider axial focusing ranges in eye tissues or simultaneous focusing of light from two axial locations in eye tissues. Eyepieces 542r and 542l may be configured with optical components without any refractive power, such as optical windows, that may be physically attached or separate from the other lenses in the system.

Light entering the right and left eyes can be reflected back through each optical path to enable optical coherence tomography. In one embodiment, the path of backreflected light originating from light source 502 can travel from each eye to eyepiece 542 to optics 540 to lens system 535 to movable mirror 530 to lens system 525 to optics 520 to coupler 515 to coupler 517 to balanced detector 518. Various calculations and logic-based processes can be completed by components 595r and 595l based on data contained in signals received from balanced detectors 518r and 518l.

As discussed previously, timing of capture of the signals received by components 595r and 595l may be controlled by other inputs, such as the k-clock input, dummy clock input, or other electrical signal. Electronics 500, 595r, and 595l may be configured to have digital signal processors (DSPs), field-programmable gate arrays (FPGAs), ASICs or other electronics to enable faster, more efficient or substantially real-time processing of signals received by components 595r and 595l. Electronics 500, 595r, and 595l may be configured with software, such as a real-time operating system, to enable rapid decisions to be made by said components.

In various embodiments not illustrated here, the eye tissues may be replaced by calibration targets that, for example, occlude the eyepieces, dispose a mirror target at various distances in front of the eyepieces, or provide an open air space for calibration. Electronics 500 may be configured to control the introduction of these non-tissue targets, such as when the eyes are not present in the optical system. In other embodiments, electronics 500 may be configured to dispose powered or moveable components of the system to various states, such as "off," "home," or "safety" at various times, such as the beginning, middle and end of a test.

Components 595r and 595l can also be configured to control light sources 585r-588r and 585l-588l which may be comprised of various light sources such as for example, laser diodes, light emitting diodes, or superluminescent diodes. In the illustrated embodiment, only four light sources 585r-588r and 585l-588l are shown. In various embodiments, different numbers of light sources 585r-588r and 585l-588l may be used and different wavelengths of light sources may be used. In one embodiment, one each of a blue-colored, green-colored, red-colored and near infrared diode can be included in the light source groups 585r-588r and 585l-588l.

In other embodiments, light sources 585r-588r and 585l-588l may be comprised of tunable light sources capable of producing numerous spectra of light for the purposes of hyperspectral imaging. For example, employing various light sources in the visible spectrum capable of producing narrow bands of light centered at characteristic peaks of absorption or reflectivity for oxyhemoglobin and deoxyhemoglobin can be used to enable hyperspectral imaging. Similarly, numerous individual light sources can be used to achieve the same effect as a light source with a tunable wavelength.

These light sources can be configured to be controlled by components 595r and 595l using, for example, pulse-width modulation, current modulation, voltage modulation, or other electrical control means. In one embodiment, the modulation frequency of at least one light source can be modified to correct for chromatic aberration from the optics between the light sources and the eye. For example, the modulation frequency of the red channel could be variably increased or decreased in different mirror positions to account for lateral chromatic spread between the red light source and other colors such as blue or green.

Light from light sources 585r-588r and 585l-588l can travel to optics 580r-583r and 580l-583l which may, for example, be focusing optics. Light from optics 580r-583r and 580l-583l can then travel to optics 575r-578r and 575l-578l which may, for example, be focusing optics. Each path of light can contain a single frequency of light, such as 450 nm, 515 nm, 532 nm, 630 nm, 840 nm, or 930 nm or multiple frequencies of light.

Each path of light from light sources 585r-588r and 585l-588l may be reflected off optics 571r-574r and 571l-574l which may, for example, be dichroic mirrors or couplers and may be specifically configured to reflect and transmit light based on their position in the optical path. For example, one optic may be configured to transmit light with a wavelength less than 500 nm and reflect light with a wavelength greater than 500 nm.

Optics 571r-574r and 571l-574l can be configured to join together light from different light sources 585r-588r and 585l-588l into a single, substantially coaxial beam of light that can travel to optics 561r and 561l. Optics 561r and 561l may be dichroic mirrors or couplers and may be configured to have a pre-defined split ratio of light entering from different directions or having different wavelengths, such as 90/10, 50/50, and 10/90.

A portion of light from optics 571r-574r and 571l-574l can be transmitted through optics 561r and 561l to sensors 566r and 566l which may, for example, be photodiodes or other components capable of sensing light. Signals from sensors 566r and 566l can be configured to be transmitted along electrical connections between sensor 566r and electrical component 595r on the right side and sensor 566l and electrical component 595l on the left side. In one embodiment, sensors 566r and 566l can be configured to monitor the total light power being emitted by light sources 585r-588r and 585l-588l.

The portion of light reflected off optics 561r and 561l from optics 571r-574 and 571l-574l can travel to lens systems 560r and 560l. Lens systems 560r and 560l may be comprised of fixed focus or variable focus lenses. In various embodiments, these lenses can be fabricated from plastic or glass. In other embodiments, these lenses may be electrowetting lenses or shape-changing lenses, such as fluid-filled lenses, that may vary their focal distance based on internal or external control mechanisms.

In one embodiment, variable focus lenses in lens systems 560r and 560l may have their focal length modified by electrical current or voltage applied to the lens systems. This control may be under the direction of electrical components 595r and 595l and it may be based on pre-determined values or be derived during operation of the system based on input received from other components of the system.

The lenses in lens systems 560r and 560l can be configured to have anti-reflective coatings, embedded temperature sensors, or other associated circuitry. Lens systems 560*r* and 560*l* may be comprised of a single lens or multiple lenses. The lenses comprising systems 560*r* and 560*l* may be present in the light path at all times or may be mechanically moved in and out of the light path by an attached motor and drive circuit under electrical control from components 595*r* and 595*l*. Configuration of lens systems 560*r* and 560 to be moveable can enable imaging at different depths in an eye tissue by introducing and removing vergence in the optical system.

Light from lens systems 560*r* and 560*l* can travel to lens systems 555*r* and 555*l*. In some embodiments, lens systems 555*r* and 555*l* can be located in their respective optical paths at all times. In other embodiments, lens systems 555*r* and 551 may be moved in and out of the optical paths based on electrical signals from components 595*r* and 595*l*.

Light from lens systems 555*r* and 555*l* can travel to movable mirrors 550*r* and 550*l*. Movable mirrors 550*r* and 550*l* may be comprised of MEMS mirrors, controlled by galvanometers, or moved by other means. Movable mirrors 550*r* and 550*l* can be comprised of a single mirror that reflects light across 2 axes, such as X and Y, can be comprised of a single mirror that reflects light across one axis only, or can be comprised of two mirrors that each reflect light across one axis only said axes being substantially perpendicular to each other.

Electrical control of mirrors 550*r* and 550*l*, which can control each axis of reflection independently, can be provided by components 595*r* and 595*l*. Mirrors 550*r* and 550*l* may have one axis of fast resonant movement, one axis of slow resonant movement, two slow axes of movement, one fast resonant axis and one slow axis of movement, or two fast resonant axes of movement.

The electronic control of mirrors 530*r* and 530*l* may be configured to enable variable amplitude deflections of mirrors 530*r* and 530*l*. For example, for a given drive frequency in a given axis, the current or voltage applied to mirrors 530*r* and 530*l* may enable larger or smaller amplitude deflections of the mirror surface, thus creating a zoom effect where the created image can be made smaller or larger.

Light from movable mirrors 550*r* and 550*l* can travel to lens systems 545*r* and 545*l*. Lens systems 545*r* and 545*l* may be configured to introduce variable amounts of optical cylinder power into the optical light paths. In one embodiment, the magnitude and axis of the cylindrical optical power introduced into the optical paths by lens systems 545*r* and 545*l* can be configured to correct an astigmatism present in an eye interfacing with this system.

Lens systems 545*r* and 545*l* can comprised of two cylindrical lenses configured to counter-rotate and co-rotate with each other, an electrically controlled variable focus, liquid filled lens, or other method of introducing cylindrical optical power into a light path. Although not illustrated here, lens systems 545*r* and 545*l* can also be located between mirrors 530*r* and 530*l* and optics 540*r* and 540*l* in the OCT light path.

Light from lens systems 545*r* and 545*l* can travel to optics 540*r* and 540*l* where it may be reflected to combine with light originating at light source 502. In one embodiment, an exit pupil expander can be disposed between moveable mirrors 550*r* and 550*l* and the eye tissues to increase the size of the exit pupil created at the eye tissue by mirrors 550*r* and 550*l*.

Light from lens systems 545*r* and 545*l* may be transmitted through eyepieces 542*r* and 542*l* after which it may enter the right and left eyes of a subject. Light transmitted through eyepieces 542*r* and 542*l* can be configured to be seen by the subject as organized light, such as in a retinal scanning display system, can be configured to be seen by the subject as video-rate imaging through modulation of light sources 585*r*-588*r* and 585*l*-588*l* by components 595*r* and 595*l*, or can be configured to broadly stimulate the eye with light such as for measurements of pupillary reactions to light stimuli.

Light from lens systems 545*r* and 545*l* can also be configured to reflect back out of the eye and through eyepieces 542*r* and 542*l*, off optics 540*r* and 540*l*, through lenses systems 545*r* and 545*l*, off moveable mirrors 550*r* and 550*l*, through lens systems 555*r*, 555*l*, 560*r*, and 560*l* and then through optics 561*r* and 561*l*. Light transmitted through optics 561*r* and 561*l* can be detected by sensors 567*r*-570*r* and 567*l*-570*l* which may, for example, be comprised of photodiodes.

In various embodiments, this light is split into predefined wavelength bands, such as 440 nm-460 nm, 510 nm-580 nm, 625 nm-635 nm, or 930 nm, by dichroic mirrors 562*r*-565*r* and 562*l*-565*l*. In other embodiments, separation of light from optics 561*r* and 561*l* into bands can be achieved by the use of filters that selectively transmit or reflect wavelength bands of interest.

In still other embodiments, separation of light from optics 561*r* and 561*l* into bands can be achieved by configuring the system with sensors 567*r*-570*r* and 567*l*-570*l* that only produce electrical signals in specifically targeted bands, such as 400-500 nm, 600-800 nm or >900 nm. Electrical signals from sensors 567*r*-570*r* and 567*l*-570*l* can travel to components 595*r* and 595*l* across electrical connections to enable imaging of tissues in the eye by sensing the light originating at light sources 585*r*-588*r* and 585*l*-588*l* backreflected in desired wavelength bands.

Figure 13:
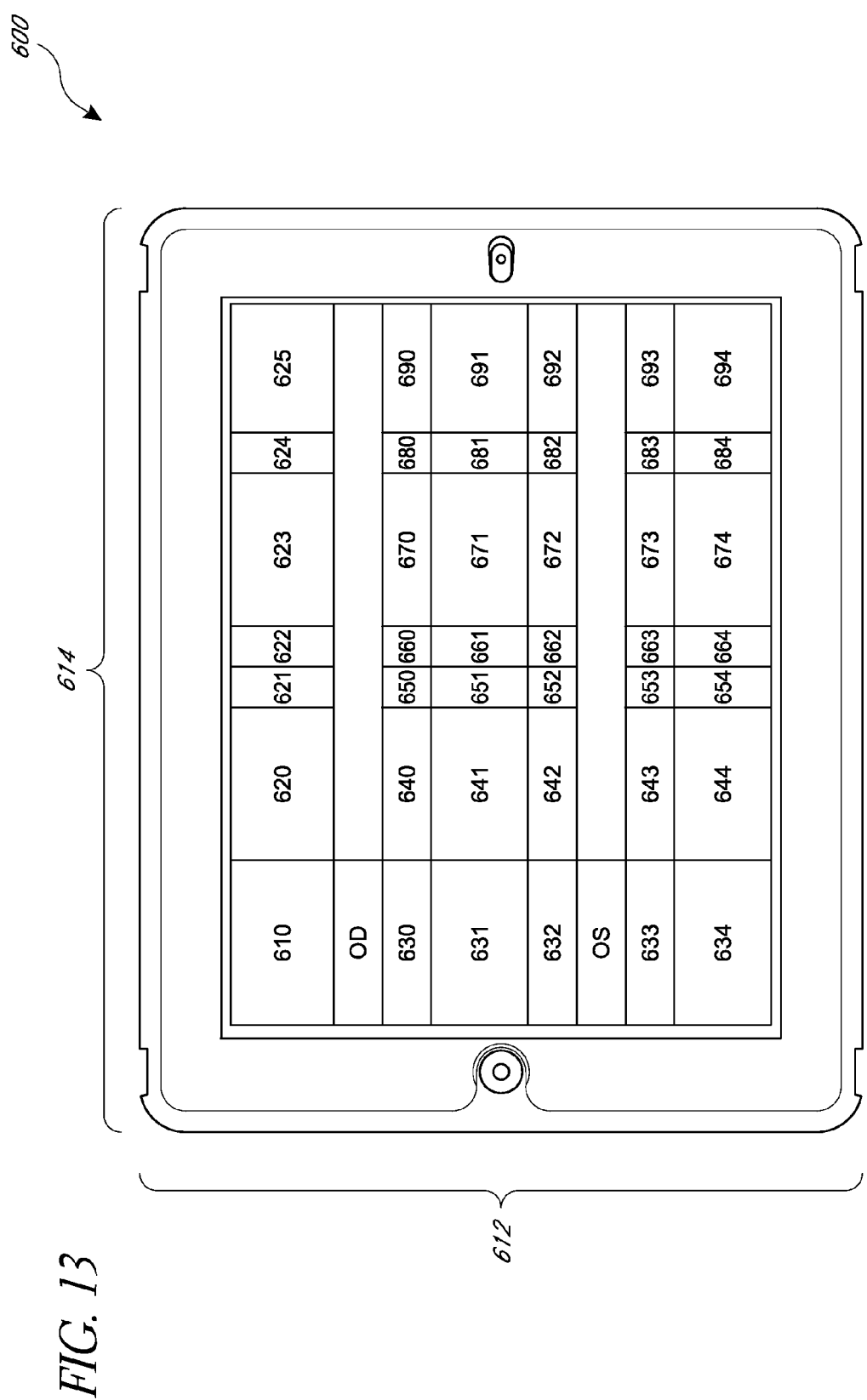
FIG. 13 schematically illustrates a display of eye examination data.

FIG. 13 shows an example of a display of eye examination data on an electronic device 600. In some embodiments, the display system enables viewing and comparing of data from two eyes of one patient across multiple tests and dates in a minimal amount of space. Accordingly, some embodiments enable the user to collapse undesirable test or date fields so as to maximize the display area of desired measurements.

Device 600 may be a portable computing platform, such as a smartphone or a tablet, or be a stationary computing platform with a display screen. Device 600 may allow touch screen operation, eye tracking operation where eye movements are interpreted as cursor movements on the device 600 itself or operation with standard computing peripherals such as a mouse and keyboard.

Data in the illustrated grid can be populated by software from a database of examination data that may, for example, include exams from many patients on many days. Accordingly, software running on device 600 can be configured to enable searching or selection of the patient whose exam data is to be displayed in the illustrated display configuration.

Software on device 600 can be configured to output exam data in a substantially tabular format comprised mainly of rows 612 and columns 614. In various embodiments, the software can be configured to include all exam data for a given date in one column 614 while all measurements from a given test can be included in a single row 612. The software can also enable preferences that allow transformation of this rule such that dates are in rows 612 and tests are in columns 614. In some embodiments, each box in the table representing an intersection of a row 612 and a column 614 can be represented as a field populated with, for example, a numerical measurement, a text value or an image. Although the fields are labeled generically in FIG. 6, it will be appreciated that a variety of data, such as numbers, text or images, can be displayed in each field.

Field 610 can be configured to contain information on the patient, such as name, date of birth, medical record number, age, gender. Although not illustrated here, field 610 may also be used to open pop-up windows that can be used to search or configure the exam display system.

Fields 620-625 can be configured to contain dates of exams for a given patient. In one embodiment, clicking of a column heading 620-625 toggles the column between collapsed and expanded configurations where data is not displayed in the collapsed configuration but data is displayed in the expanded configuration. In FIG. 6, columns 620, 623 and 625 demonstrate expanded fields while columns 621, 622 and 624 represent collapsed fields. Thus, the fields in the collapsed columns 621, 622, 624 may be collapsed. For example, fields 650, 651, 652, 653, 654 may be collapsed when column 621 is collapsed. The software can be configured to allow users to toggle this display setting with, for example, a simple click of a column heading or other selection process.

Fields 630-634 can be configured to contain individual tests conducted on a given patient. In one embodiment, clicking of a row heading 630-634 toggles the row between collapsed and expanded configurations where data is not displayed in the collapsed configuration but data is displayed in the expanded configuration. In FIG. 6, rows 631 and 634 demonstrate expanded fields while rows 630, 632 and 633 represent collapsed fields. Thus, the fields in the collapsed rows 630, 632, 633 may be collapsed. For example, fields 640, 650, 660, 670, 680, and 690 may be collapsed when row 630 is collapsed. The software can be configured to allow users to toggle this display setting with, for example, a simple click of a row heading or other selection process.

In FIG. 13, it can be appreciated that two special rows can exist corresponding to the right (OD) and left (OS) eye headings. The software can be configured to collapse or expand all tests for a given eye when that row heading, such as OD or OS, is clicked or otherwise selected.

Referring to FIG. 13, fields 641, 644, 671, 674, 691, and 694 can be configured to display data, such as numbers, text or images. In one embodiment, display of images in these fields enables the user to click on the images to bring up a larger window in which to view the images. In another embodiment, display of numbers in these fields enables the user to click on the numbers to bring up a graph of the numbers, such as graph over time with the dates in the column headers as the x-axis and the values in the rows as the y values.

The software can be configured to show collapsed fields (e.g. field 640, 650, 660, 651, 661) in a different color or in a different size. The software can also be configured to display scroll bars when fields extend off the display screen. For example, if more tests exist in the vertical direction than can be displayed on a single screen, the software can be configured to allow panning with finger movements or scrolling with, for example, vertical scroll bars. The software can be configured to enable similar capabilities in the horizontal direction as well.

What is claimed is:

1. A mask, comprising:
   a distal sheet member having one or more optically transmissive sections;
   a proximal inflatable member having a rear concaved surface that faces a first patient's face when in use, wherein the rear concaved surface is configured to conform to contours of the first patient's face;
   the inflatable member having two cavities therein, wherein each of the two cavities is aligned with one of the patient's eyes when in use, wherein the two cavities extend from the rear concaved surface toward the distal sheet member such that the two cavities define two openings on the rear concaved surface;
   wherein the rear concaved surface is configured to seal against the first patient's face such that the first patient's eyes are aligned with the two cavities, so that the rear concaved surface forms seals around a peripheral region of the first patient's eye sockets that inhibit flow of fluid into and out of the cavities;
   an ocular port providing access to at least one of the two ocular cavities for fluid flow into and out of the at least one of the two ocular cavities; and
   an inflation port providing access to inflate the inflatable member.

2. The mask of claim 1, wherein the rear concaved surface is configured to conform to the contours of the first patient's face with inflation of the inflatable member via the inflation port.

3. The mask of claim 1, wherein the inflatable member is underinflated, wherein the rear concaved surface is configured to conform to the contours of the first patient's face with inflation of the underinflated inflatable member via the inflation port.

4. The mask of claim 1, wherein the rear concaved surface is configured to conform to the contours of the first patient's face with application of negative pressure to the inflatable member via the inflation port.

5. The mask of claim 1, further comprising particulate matter disposed within the inflatable member, wherein the particulate matter is configured to pack together with application of negative pressure to the inflatable member via the inflation port, so that the rear concaved surface conforms to the contours of the first patient's face.

6. The mask of claim 1, wherein the rear concaved surface is configured to conform to contours of a second patient's face, wherein a contour of the second patient's face is different from a contour of the first patient's face.

7. The mask of claim 1, further comprising a lip extending into at least one of the two cavities from a perimeter of at least one of the two openings, the lip having distal ends curving toward the distal sheet member in a default position, the distal ends configured to move rearwardly such that the lip seals against the user's face upon introduction of positive pressure into the at least one of the two cavities.

8. The mask of claim 1, wherein the distal sheet member is configured to interface with a medical device.

9. The mask of claim 8, wherein the medical examination device is an eye exam device.

10. The mask of claim 1, wherein the mask is configured to couple with a docking portion on a medical device.

11. The mask of claim 1, wherein the inflation port and the ocular port are configured to couple with conduit ends on a medical device.

12. The mask of claim 11, wherein the ocular port and the inflation port are configured to couple with the conduit ends on the medical device simultaneously.

13. The mask of claim 1, wherein the mask is deflatable.

14. The mask of claim 1, wherein the inflatable member is opaque.

15. A mask comprising:
   a distal sheet member having one or more optically transmissive sections;
   a proximal pre-inflated member having a rear concaved surface that faces a first patient's face when in use, wherein the rear concaved surface is configured to conform to contours of the first patient's face;
   the pre-inflated member having two cavities therein, each of the two cavities being aligned with one of the patient's eyes when in use, wherein the two cavities extend from the distal sheet member to the rear concaved surface such that the two cavities define openings on the rear concaved surface;

wherein the rear concaved surface is configured to seal against the first patient's face such that the first patient's eyes are aligned with the two cavities, so that the rear concaved surface forms seals around a peripheral region of the first patient's eye sockets that inhibit flow of fluid into and out of the two cavities; and an ocular port providing access to at least one of the two ocular cavities for fluid flow into and out of the at least one of the two ocular cavities.

16. A system, comprising:
a medical device housing containing a medical instrument therein, wherein the medical device housing is configured to interface with a mask;
a pump assembly comprising:
one or more conduits;
a pump configured to provide fluid to one or more conduit ends via the one or more conduits; and
a pressure sensor configured to sense a pressure in an ocular cavity formed in an inflatable member of the mask; and
a processor in electronic communication with the pump and the pressure sensor, wherein the processor is configured to:
receive the pressure in the ocular cavity; and
control operation of the pump.

17. The system of claim 16, further comprising conduit ends on the medical device housing, wherein the conduit ends are configured to couple with a port on the mask.

18. The system of claim 16, wherein the medical device housing comprises a docking portion configured to couple with the mask.

19. The system of claim 16, wherein the processor is configured to control operation of the pump based at least in part on the pressure in the ocular cavity.

20. The system of claim 16, wherein the processor is configured to determine an ocular measurement based at least in part on the pressure in the ocular cavity.

21. The system of claim 16, further comprising a valve in fluid communication with the pump and in electronic communication with the processor, wherein the processor is configured to change a state of the valve.

22. A method, comprising:
receiving, by a computing system, patient distance information from a device configured to provide distance information,
wherein the distance information is indicative of a distance between a patient and a medical device,
wherein the patient is coupled to a mask comprising an inflatable chamber; and
modulating, by the computing system, inflation or deflation of the inflatable chamber based at least in part on a desired distance.

23. The method of claim 22, further comprising determining, by the computing system, the desired distance based at least in part on a parameter of a medical examination, treatment, or diagnosis.

24. The method of claim 22, wherein the device configured to provide distance information is a sensor.

25. The method of claim 22, wherein the device configured to provide distance information is an optical coherence tomography device.

26. A method of taking ocular measurements, comprising:
changing, by a computing system, a pressure in an ocular cavity formed in an inflatable member of a mask;
receiving, by the computing system, an indication of the pressure in the ocular cavity; and
determining, by the computing system, a change to an ocular measurement in response to the change in the pressure in the ocular cavity.

27. The method of claim 26, wherein the ocular cavity defines an opening on a rear surface of the mask, wherein the rear surface is configured to seal against a patient's face such that the patient's eye is aligned with the cavity, so that the rear surface forms seals around a peripheral region of the patient's eye socket that inhibit flow of fluid into and out of the cavity.

28. The method of claim 26,
wherein changing the pressure in the ocular cavity comprises controlling operation of a pump and/or changing a state of a valve;
wherein the pump, the valve, and the mask are in fluid communication.

29. The method of claim 26, wherein determining an ocular measurement comprises processing data received from optical imaging components.

* * * * *